(12) United States Patent
Moll

(10) Patent No.: US 9,937,026 B2
(45) Date of Patent: Apr. 10, 2018

(54) SYSTEM AND METHOD FOR TEETH CLEANING

(71) Applicant: Frederic H. Moll, San Francisco, CA (US)

(72) Inventor: Frederic H. Moll, San Francisco, CA (US)

( * ) Notice: Subject to any disclaimer, the term of this patent is extended or adjusted under 35 U.S.C. 154(b) by 0 days.

(21) Appl. No.: 15/665,313

(22) Filed: Jul. 31, 2017

(65) Prior Publication Data

US 2017/0325921 A1    Nov. 16, 2017

Related U.S. Application Data

(63) Continuation of application No. 15/178,995, filed on Jun. 10, 2016, now abandoned, which is a
(Continued)

(51) Int. Cl.
*A61C 17/16* (2006.01)
*A61C 17/22* (2006.01)
(Continued)

(52) U.S. Cl.
CPC ........... *A61C 17/228* (2013.01); *A46B 9/045* (2013.01); *A46B 13/023* (2013.01);
(Continued)

(58) Field of Classification Search
CPC . A61C 17/228; A61C 17/0211; A61C 17/221; A61C 17/222; A61C 17/3481; A46B 9/045; A46B 13/023
See application file for complete search history.

(56) References Cited

U.S. PATENT DOCUMENTS 3,380,446 A    4/1968  Martin
3,401,690 A *  9/1968  Martin ................... A61C 17/20
                                                            433/119
(Continued)

FOREIGN PATENT DOCUMENTS

CN    101053535    10/2007
EP     1506746      2/2005
(Continued)

OTHER PUBLICATIONS

Amendment to Non-Final Office Action filed May 5, 2014 for U.S. Appl. No. 13/332,312 (11 pages).
(Continued)

*Primary Examiner* — Shay Karls
(74) *Attorney, Agent, or Firm* — Vista IP Law Group, LLP

(57) ABSTRACT

Embodiments are described wherein a system for brushing the teeth of a person comprises a master input device; a flexible teeth tray configured to at least partially encapsulate one or more of the teeth in a flexible substrate material, the flexible teeth tray comprising one or more vibratory transducers removably coupled to one or more brushing panels; and a controller operatively coupled to the master input device and the one or more vibratory transducers; wherein subject to an input from the master input device, the controller is configured to cause reciprocating brushing motion of the one or more brushing panels against a surface of the one or more encapsulated teeth, to clean the one or more teeth.

20 Claims, 34 Drawing Sheets

Related U.S. Application Data continuation of application No. 14/846,304, filed on Sep. 4, 2015, now abandoned, which is a continuation of application No. 14/481,736, filed on Sep. 9, 2014, now abandoned, which is a continuation of application No. 13/332,312, filed on Dec. 20, 2011, now Pat. No. 8,856,997.

(60) Provisional application No. 61/424,873, filed on Dec. 20, 2010, provisional application No. 61/522,832, filed on Aug. 12, 2011.

(51) Int. Cl.
*A46B 13/02* (2006.01)
*A61C 17/02* (2006.01)
*A46B 9/04* (2006.01)
*A61C 17/34* (2006.01)

(52) U.S. Cl.
CPC ........ *A61C 17/0211* (2013.01); *A61C 17/221* (2013.01); *A61C 17/222* (2013.01); *A61C 17/3481* (2013.01)

(56) References Cited

U.S. PATENT DOCUMENTS

| | | | |
|---|---|---|---|
| 4,237,574 | A | 12/1980 | Kelly et al. |
| 5,443,386 | A | 8/1995 | Viskup |
| 6,223,376 | B1 | 5/2001 | Lee |
| 7,044,737 | B2 * | 5/2006 | Fu ................. A61C 17/0211 433/119 |
| 2005/0196725 | A1 | 9/2005 | Fu |
| 2010/0160838 | A1 | 6/2010 | Krespi |

FOREIGN PATENT DOCUMENTS

| | | |
|---|---|---|
| JP | 200457315 | 2/2004 |
| JP | 2008173144 | 7/2008 |
| WO | WO 2007025244 | 3/2007 |
| WO | WO 2007121760 | 11/2007 |

OTHER PUBLICATIONS

Non-Final Office Action dated Nov. 4, 2013 for U.S. Appl. No. 13/332,312 (17 pages).
Notice of Allowance dated Jun. 11, 2014 for U.S. Appl. No. 13/332,312 (8 pages).
Non-Final Office Action dated Mar. 4, 2015 for U.S. Appl. No. 14/481,736 (7 pages).
Final Office Action dated Dec. 10, 2015 for U.S. Appl. No. 14/846,304 (8 pages).
Final Office Action dated Feb. 1, 2017 for U.S. Appl. No. 15/178,995 (7 pages).
PCT International Search Report and Written Opinion for PCT/US2011/066315 Filed Dec. 20, 2011, Applicant Frederic H. Moll, Forms PCT/ISA/210, 220 and 237 dated Jul. 27, 2012 (20 pages).
Office Action and Translation provided by Foreign Associate in Japanese Patent Application No. 2016-100350 dated Feb. 24, 2017, (13 pages).
Response to 161 Communication in European Application No. EP11808796.4 dated Mar. 6, 2014 (10 pages).
Translation provided by Foreign Associate of Office Action in Chinese Patent Application No. 201180067898.9 dated Feb. 27, 2015 (4 pages).
Response to Office Action in Chinese Application No. 201180067898.9 dated Sep. 14, 2015 (5 pages).
Office Action in Chinese Application No. 201180067898.9 dated Dec. 3, 2015 (5 pages).
Response to OA in Chinese Application No. 201180067898.9 dated Apr. 18, 2016 (5 pages).
Office Action in Chinese Application No. 201180067898.9 dated Jul. 18, 2016 (5 pages).
Notice of Allowance in Japanese Patent Application No. 2013-546349 dated Oct. 26, 2016 (3 pages).
Response to Office Action in Chinese Application No. 201180067898.9 dated Dec. 2, 2016 (5 pages).
Examination Report in Australian Application No. 2016206343 dated Feb. 2, 2017 (4 pages).
Official Action in Japanese Patent Application No. 2013-546349 and Translation provided by Foreign Associate dated Nov. 19, 2015 (7 pages).
Response to Official Action in Japanese Patent Application No. 2013-546349 dated May 19, 2016 (7 pages).
Response to Official Action in Japanese Patent Application No. 2016-100350 dated Aug. 17, 2017 (4 pages).
Communication under Rule 71(3) in European Patent Application No. 11808796.4 dated Aug. 7, 2017 (62 pages).
Office Action in Canadian Application No. 2822286 dated May 25, 2017 (3 pages).
Response to Office Action in Canadian Application No. 2822286 dated Aug. 2, 2017 (4 pages).
Response to Examination Report in Australian Application No. 2016206343 dated Aug. 2, 2017 (23 pages).
Notice of Allowance in Australian Application No. 2016206343 dated Aug. 29, 2017 (67 pages).
Voluntary Amendment in Australian Application No. 2016206343 dated Nov. 13, 2017 (5 pages).
Office Action and Translation provided by Foreign Associate in Chinese Application No. 201180067898.9 dated Mar. 20, 2017 (5 pages).
Response to Office Action in Chinese Application No. 201180067898.9 dated May 18, 2017 (19 pages).
Response to Office Action in Chinese Application No. 201180067898.9 dated Jul. 28, 2017 (3 pages).
Office Action in Chinese Application No. 201180067898.9 dated Jun. 20, 2017 (20 pages).
Notice of Grounds of Rejection in Korean Application No. 10-2013-7019279 dated Oct. 23, 2017 (14 pages).
Notice of Allowance in Canadian Patent Application No. 2822286 dated Nov. 16, 2017 (1 page).
Response to Communication under Rule 71(3) in European Patent Application No. 11808796.4 dated Dec. 4, 2017.

\* cited by examiner

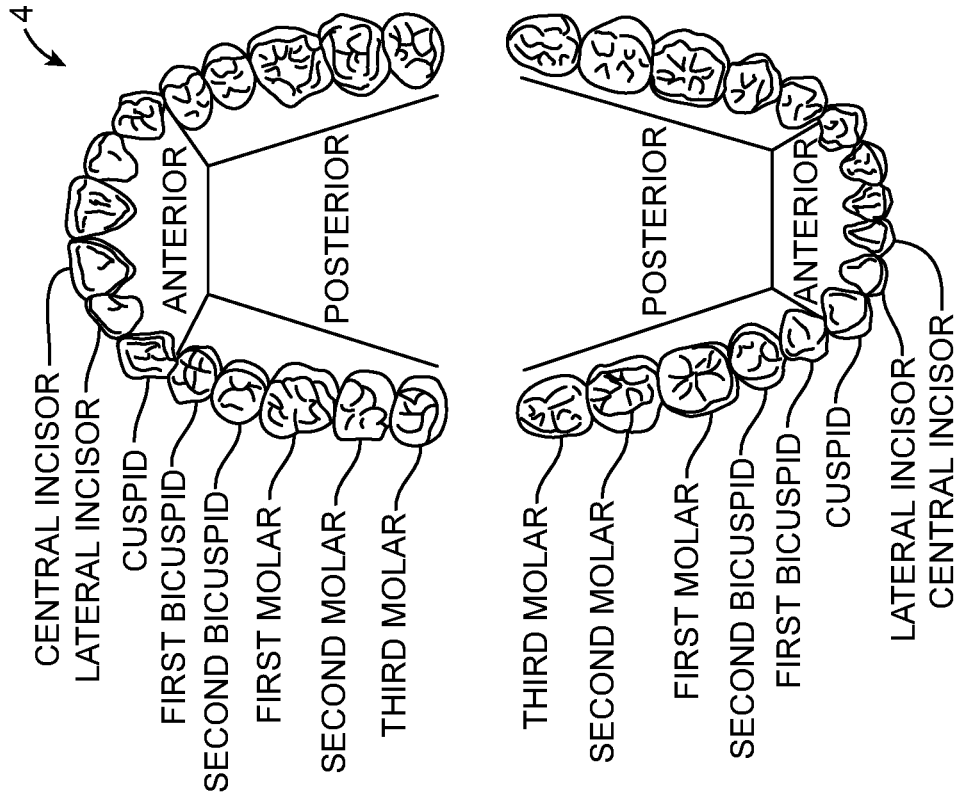
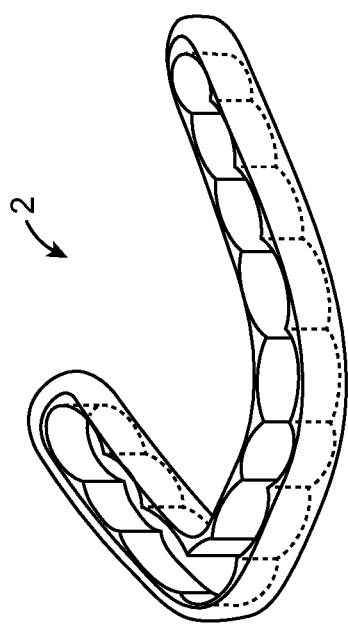
FIG. 1B
FIG. 1A

Sample Program 1 (approx 1 minute):

1. Upper Left for 10 seconds;
2. cycle change signal buzz;
3. Upper Center for 10 seconds;
4. cycle change signal buzz;
5. Upper Right for 10 seconds;
6. cycle change signal buzz;
7. Lower Left for 10 seconds;
8. cycle change signal buzz;
9. Lower Center for 10 seconds;
10. cycle change signal buzz;
11. Lower Right for 10 seconds;
12. cycle change signal buzz.

Sample Program 4 (approx 20 seconds): — 78

1. All Upper and Lower for 10 seconds with transducers at first frequency setting;

2. All Upper and Lower for 10 seconds with transducers at second frequency setting;

3. Cycle change signal buzz.

Figure 5A

Sample Program 5 (approx 30 seconds):

1. All Upper and Lower for 10 seconds with transducers at first frequency setting;

2. All Upper and Lower for 10 seconds with transducers at second frequency setting;

3. All Upper and Lower for 10 seconds with transducers at first frequency setting;

4. Cycle change signal buzz.

Sample Program 6 (approx 30 seconds):

1. All Upper and Lower for 10 seconds with transducers at first frequency setting;

2. All Upper and Lower for 10 seconds with transducers at second frequency setting;

3. All Upper and Lower for 10 seconds with transducers at third frequency setting;

4. Cycle change signal buzz.

SYSTEM AND METHOD FOR TEETH CLEANING

RELATED APPLICATION DATA

The present application is a continuation of U.S. patent application Ser. No. 15/178,995, filed on Jun. 10, 2016, which is a continuation of U.S. patent application Ser. No. 14/846,304, filed on Sep. 4, 2015, which is a continuation of U.S. patent application Ser. No. 14/481,736, filed on Sep. 9, 2014, which is a continuation of U.S. patent application Ser. No. 13/332,312, filed on Dec. 20, 2011 and issued on Oct. 14, 2014 as U.S. Pat. No. 8,856,997, which claims the benefit under 35 U.S.C. § 119 to U.S. provisional patent application Ser. No. 61/424,873, filed Dec. 20, 2010 and 61/522,832, filed Aug. 12, 2011. The foregoing applications are hereby incorporated by reference into the present application in their entirety.

FIELD OF THE INVENTION

The present invention relates generally to dental systems and processes, and specifically to teeth cleaning consumer products.

BACKGROUND

The process of cleaning one's teeth with a conventional toothbrush can be time consuming and inadequate, depending upon the quality of the brushing device and the operator thereof. Several technologies have been developed to assist with the process of tooth brushing or tooth cleaning, including water jet type devices, electromechanical tooth brushing systems of various sorts, and professional teeth cleaning tools, such as those which involve high frequency vibration of a pick type end effector to assist a dentist or hygienist with a process known conventionally in America as a "teeth cleaning". Notwithstanding the currently-available technologies, most consumers brush their teeth manually for one or more times per day for several minutes with a conventional toothbrush. There is a need for more efficient and effective tooth brushing or tooth cleaning technologies that are accessible to consumers.

BRIEF DESCRIPTION OF THE DRAWINGS

FIG. 1A depicts a conventional bite-guard type of flexible tray.

FIG. 1B depicts the human teeth that generally need cleaning on a daily basis.

FIGS. 5A-5C illustrate various programming configurations for embodiments of the subject system for automating aspects of the tooth brushing process.

FIGS. 9B and 9C are partial sectional views of the structure depicted in FIG. 9A.

SUMMARY

Figure 2A:
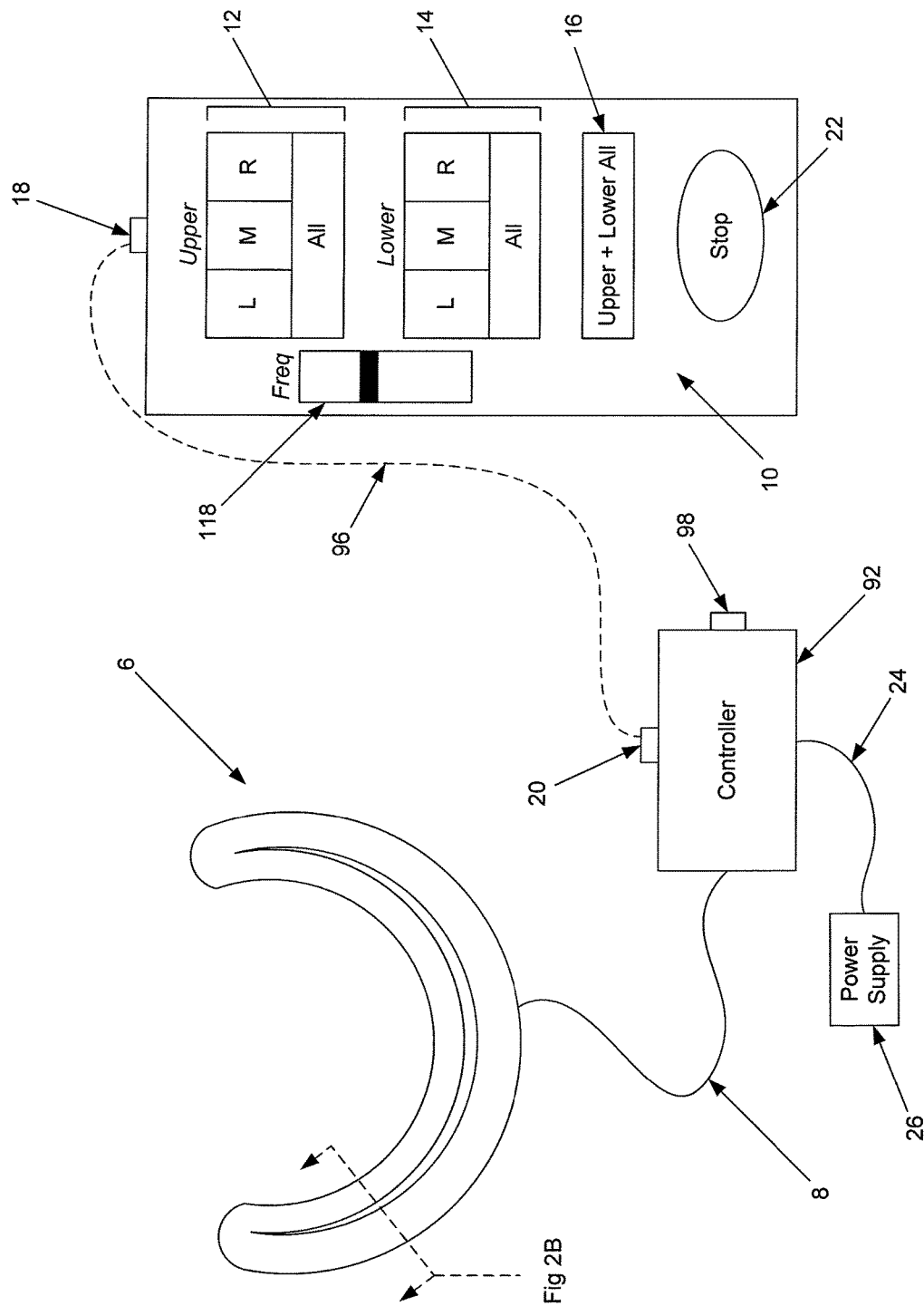
FIG. 2A illustrates one embodiment of a system for automating aspects of the tooth brushing process.

One embodiment is directed to a system for brushing the teeth of a person, comprising: a flexible teeth tray configured to at least partially encapsulate one or more of the teeth in a flexible substrate material, the flexible teeth tray comprising one or more vibratory transducers removably coupled to one or more brushing panels; and a controller operatively coupled to the one or more vibratory transducers; wherein subject to an input from an operator, the controller is configured to cause reciprocating brushing motion of the one or more brushing panels against a surface of the one or more encapsulated teeth, to clean the one or more teeth. The master input device may comprise a handheld remote control interface. The handheld remote control interface may be operatively coupled to the controller with a wireless interface. The handheld remote control interface may be operatively coupled to the controller with a wired interface. The one or more vibratory transducers may be operatively coupled to the controller with a wired interface. At least a portion of the wired interface may be encapsulated in the flexible substrate material. The one or more vibratory transducers may comprise piezoelectric transducers. The piezoelectric transducers may be configured to oscillate at ultrasonic frequencies. The one or more brushing panels may comprise a substrate panel coupled to a brushing media. The substrate panels may be removably coupled to the one or more vibratory transducers. An interference fit clip fitting may be utilized to removably couple the substrate panels to the vibratory transducers. The substrate panels may be fixedly coupled to the one or more vibratory transducers. The brushing media may comprise one or more flexible bristles. The one or more flexible bristles may comprise a natural fiber. The one or more flexible bristles may comprise a manufactured fiber. The manufactured fiber may comprise a polymer selected from the group consisting of: nylon, polypropylene, polyethylene, polyethylene terephthalate, and co-polymers thereof. The flexible substrate material may comprise a polymer. The polymer may comprise MC10 (RTM). At least of the one or more panels may be interfaced with an inside surface of a tooth. At least one of the one or more panels may be interfaced with an outside surface of a tooth. At least one of the one or more panels may be interfaced with a biting surface of a tooth.

Another embodiment is directed to a system for brushing the teeth of a person, comprising: a flexible teeth tray configured to at least partially encapsulate one or more of the teeth in a flexible substrate material, the flexible teeth tray comprising one or more shockwave electrode pairs configured to controllably transmit shockwaves to the one or more teeth to disrupt material which may be coupled to the one or more teeth; and a controller operatively coupled to the one or more shockwave electrode pairs; wherein subject to an input from an operator, the controller is configured to cause one or more shockwaves to be directed against one or more surfaces of the one or more encapsulated teeth, to clean the one or more teeth. The flexible teeth tray may be configured to clean each of the teeth of the upper or lower jaw, the tray comprising one or more shockwave electrode pairs positioned adjacent each of the teeth of the upper or lower jaw. The one or more shockwave electrode pairs may be at least partially encapsulated in a transmissive material configured to isolate the one or more teeth from the one or more shockwave electrode pairs, while also transmitting shockwaves generated at the one or more shockwave electrode pairs to the one or more teeth. The transmissive material may comprise a fluid. The transmissive material may comprise a viscous gel material.

DETAILED DESCRIPTION

Figure 2B:
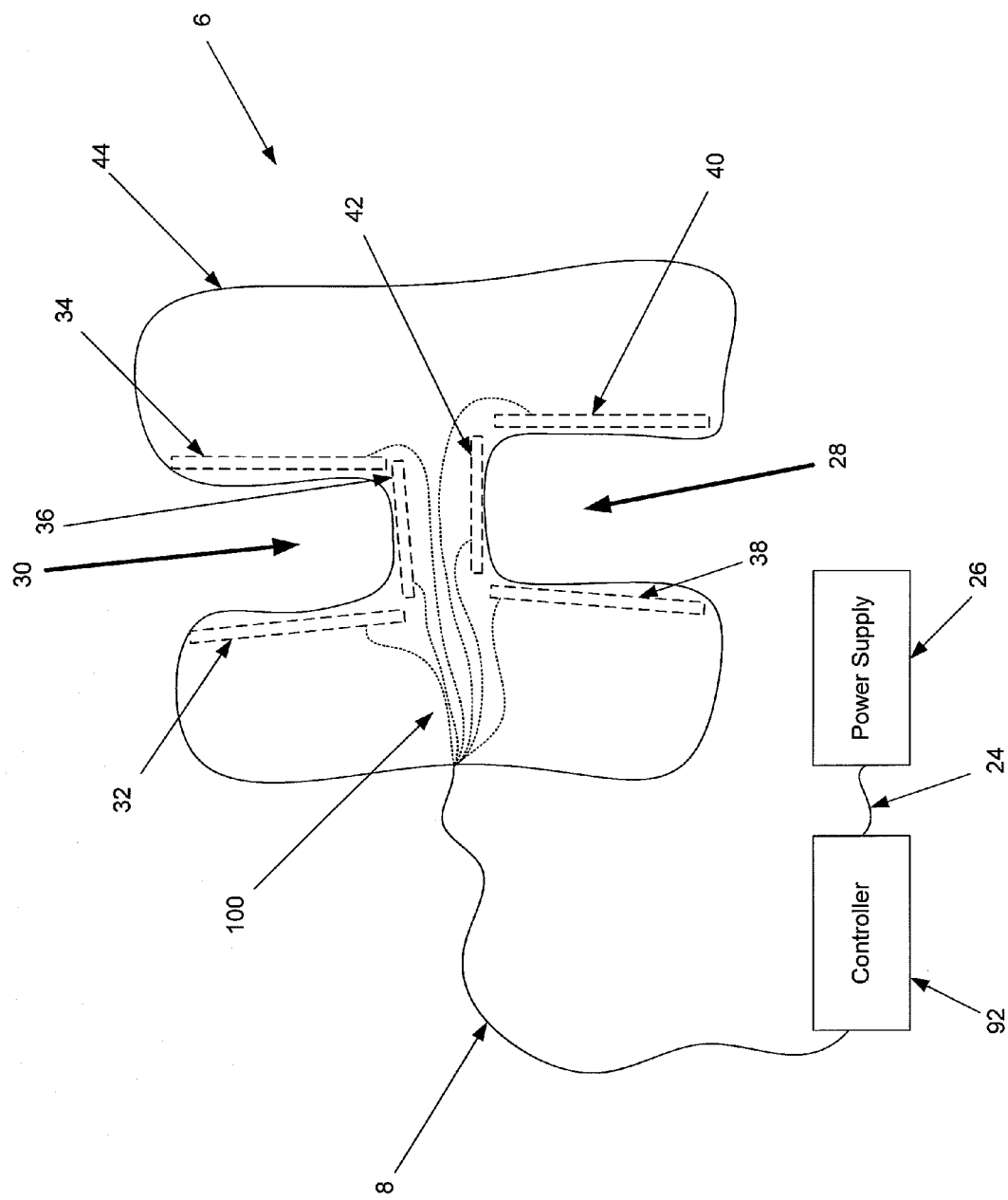
FIG. 2B illustrates a close-up cross sectional view of one embodiment of a system for automating aspects of the tooth brushing process.

Referring to FIG. 1A, flexible dental trays (2) are utilized for various applications on modern dentistry, including bite-guard applications, grinding prevention applications, and impact sport injury prevention applications. They may be custom molded to fit a particular patient's teeth, or may be configured in one or more off-the-shelf sizes to fit an average human dental configuration, as shown in FIG. 1B. Referring to FIG. 2A, a teeth brushing assembly (6) comprising a flexible dental tray with embedded brushing features is depicted. Referring to the cross sectional view of FIG. 2B, a flexible substrate material (44) is formed into a cross sectional shape configured to accommodate interdigitation of an upper tooth (30) as well as a lower tooth (28). The fit of the teeth into these geometric accommodations, or "slots", may be a slight interference fit, or may be a slightly loose fit. Too tight an interference fit is not preferred because it may prevent relative motion of the brushing panels or pads (32, 34, 36, 38, 40, 42) relative to the teeth, as described below. As shown in FIG. 2B, a power supply (26) is operatively coupled, via a wire lead (24) in the depicted embodiment, to a controller (92), which is operatively coupled to the depicted plurality of brushing pads (32, 34, 36, 38, 40, 42) that are movably coupled to the flexible substrate material (44) of the tray assembly (6), in this embodiment by one or more wire leads (8), the distal portions of which (100) may be at least partially encapsulated within the flexible substrate material (44). As described in further detail below, when the power supply (26) is activated and the controller (92) is configured to operate the brushing pads (32, 34, 36, 38, 40, 42), the brushing pads (32, 34, 36, 38, 40, 42) cyclicly motion relative to the substrate material (44) and the teeth (i.e., generally in a motion at least somewhat co-planar with the plane of the associated tooth surface), to brush films, deposits, plaque, and other materials from the teeth—in a high-frequency tooth brushing configuration. Referring again to FIG. 2B, with the depicted embodiment, the tooth that becomes engaged in the upper slot (30) will have a front brushing pad (32) to engage the front surface of the upper tooth, a rear brushing pad (34) to engage the rear surface of the upper tooth, a top (or "biting surface") brushing pad (36) to engage the top surface of the upper tooth, a front brushing pad (38) to engage the front surface of the lower tooth engaged into the lower slot (28), a rear brushing pad (40) to engage the rear surface of the lower tooth, and a top (or "biting surface") brushing pad (42) to engage the top surface of the lower tooth. In other embodiments, one or more brushing pads may be configured to address the surfaces of one or more adjacent teeth.

Referring back to FIG. 2A, a hand held master input device (10), such as a remote controller console with a plurality of buttons, may be utilized to control the system. The depicted master input device (10) comprises a stop button (22), a frequency of vibration control slider (118), and mode control buttons (12, 14), in this embodiment configured to allow the operator to select various different upper teeth engagement patterns (for example, only the left upper, only the middle upper, only the right upper, or various combinations thereof—including all of the uppers at once; similarly the lower teeth may be controllably engaged). One control button (16) conveniently allows for full engagement of all brushing pads simultaneously. A controller interface (18) may comprise a wired port or an antenna, depending upon whether the master input device is operatively coupled (96) to the controller with a wired or a wireless configuration. Similarly, the controller interface (20) may comprise a wired port or an antenna, depending upon whether the master input device is operatively coupled (96) to the controller with a wired or a wireless configuration. The controller (92) also features a programming interface (98) to allow various teeth cleaning programs to be loaded or modified into memory that comprises the controller (92).

Figure 2C:
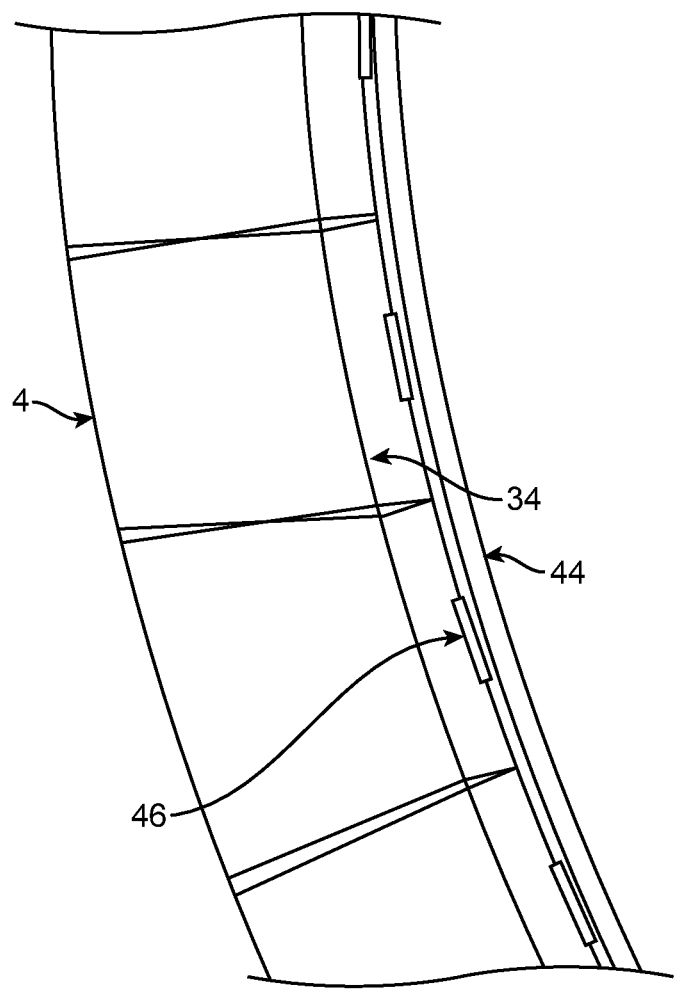
FIGS. 2C and 2D depict close-up side views of one embodiment of a system for automating aspects of the tooth brushing process.
Figure 2D:
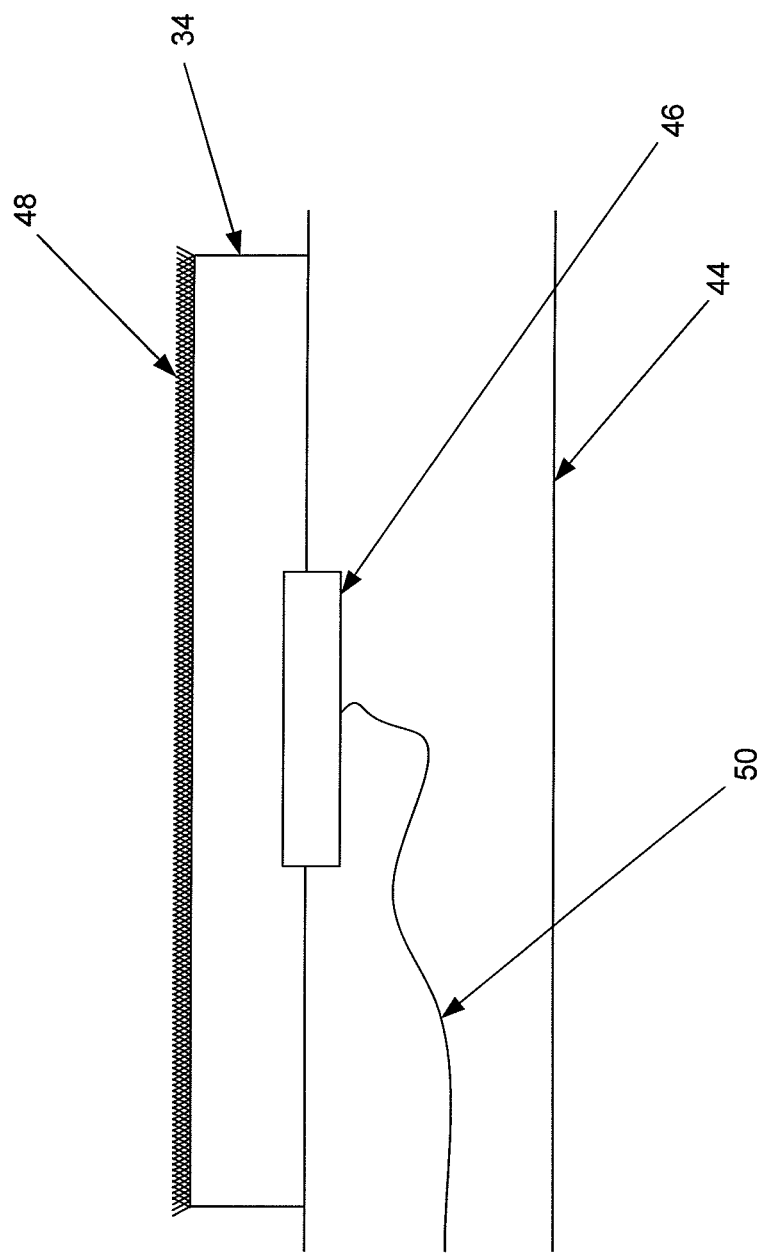

Referring to FIGS. 2C and 2D, further details of an embodiment such as that depicted in FIGS. 2A and 2B are illustrated. FIG. 2C shows a series of teeth (4) captured in a tray (or temporarily partially encapsulated in or coupled to the tray) being engaged by a series of brushing pads (34), each of which may be removably coupled to a vibratory transducer (46) which is embedded into the flexible substrate material (44). In another embodiment, the brushing pads (34) may be fixedly coupled to the transducer (46) and configured to be disposed of at the same time as the transducer (46) and substrate (44) constructs. In other words, in a first embodiment, the pads (34) are intended to be more disposable than the other structures; in a second embodiment, the structures that are designed to enter the patient's mouth are intended to be disposed of together. The illustrated embodiment shows one brushing pad per tooth, but as noted above, other embodiments may feature brushing pads configured to address more than one adjacent tooth. Referring to FIG. 2D, a close up side view shows a single vibratory transducer (46) coupled to the flexible substrate material (44), and also coupled to a brushing pad (34) which comprises a brushing surface or brushing interface (48). Preferably the brushing interface comprises a textured surface configured to remove plaque, films, and other materials from the surface of a tooth. In one embodiment, the brushing interface (48) comprises a brushing media such as series of bristles comprising natural fibrous materials, or polymeric fibrous materials, such as nylon, polypropylene, polyethylene, polyethylene terephthalate, and/or co-polymers thereof, which are commonly used in human consumer products. When the transducer is operated, via a current transmitted through the control lead (50), the transducer is configured to vibrate relative to the substrate tray around it (it remains coupled to the tray, but produces localized micromotion vibrations), and since the transducer is directly coupled to the brushing pads, relative motion is produced between the brushing pads (34) and the substrate tray (44). The brushing pads may be disposable or replaceable, and may be removably coupled to the transducers with a clip-on "temporarily fixedly coupled" type of interface involving a small interference fit clip or the like. The pads (34) may be planar, convex, concave, saddle-shaped, or have custom surface shapes configured to specifically address certain teeth or dental geometries. The transducers may be piezoelectric transducers, and may be configured to operate at frequencies in the ultrasonic range, or in other ranges. The flexible substrate material may comprise a polymer, and maybe a conformal polymer configuration, such as that available under the tradename "MC10", which is particularly well suited for embedding wire leads, as shown in FIG. 2B.

Figure 3:
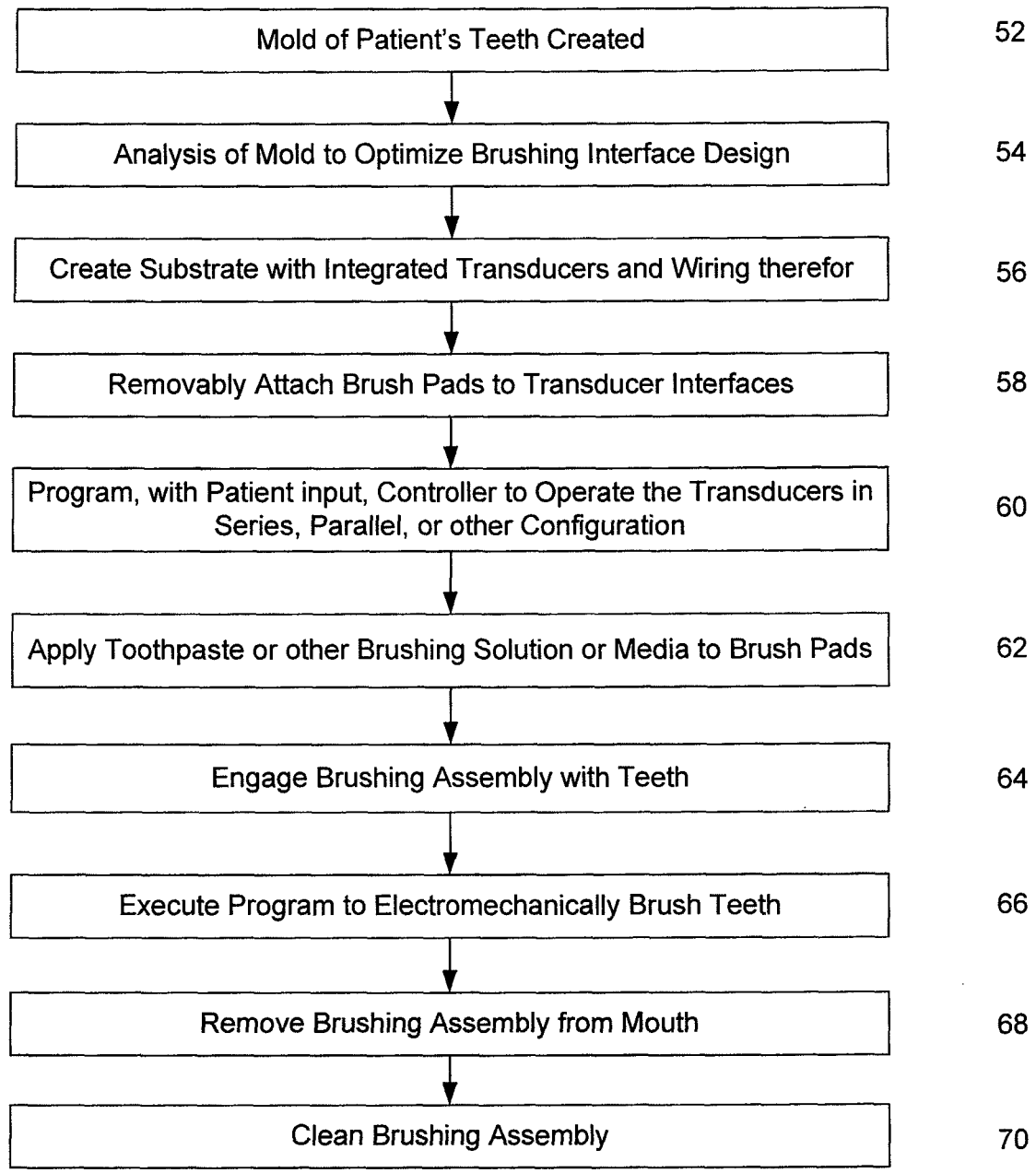
FIG. 3 illustrates a process for cleaning teeth in accordance with one embodiment of a system for automating aspects of the tooth brushing process.

Referring to FIG. 3, in one process embodiment, a mold of a patient's teeth may be created (52), followed by analysis of the mold to optimize a brushing interface design (i.e., optimize the surface shapes of the panels or pads, the shape of the tray, the bristle materials, etc) (54). A tray may be created comprising a substrate material having integrated transducers and related wiring (56). In another embodiment, an off-the-shelf tray size or model may be selected. Brush pads may be removably attached to the transducer interfaces (58), the controller programmed and configured (60), toothpaste or other brushing solution applied to the pads (62), and the assembly engaged (i.e., by placing it into the mouth and biting down) (64) so that a program or other control paradigm may be executed and the teeth cleaned (66). Subsequently the tray assembly may be removed from the mouth (68) and cleaned (70), for example, by placing the assembly in a bath or stream of clean water and briefly operating the transducers to shake loose any deposits.

Figure 4A:
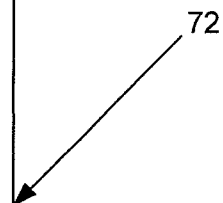
FIGS. 4A-4C illustrate various programming configurations for embodiments of the subject system for automating aspects of the tooth brushing process.
Figure 4B:
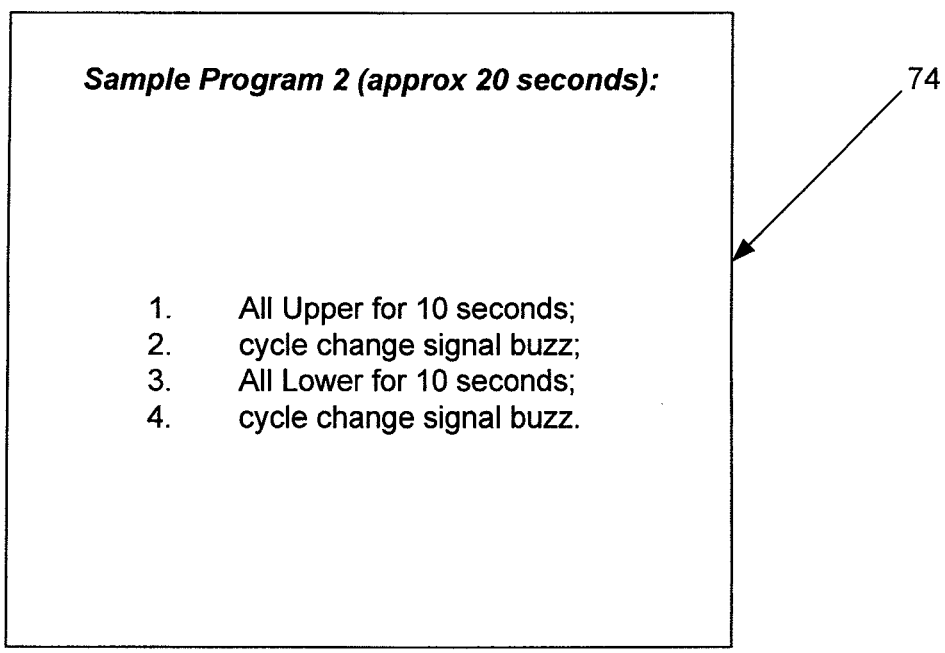
Figure 4C:
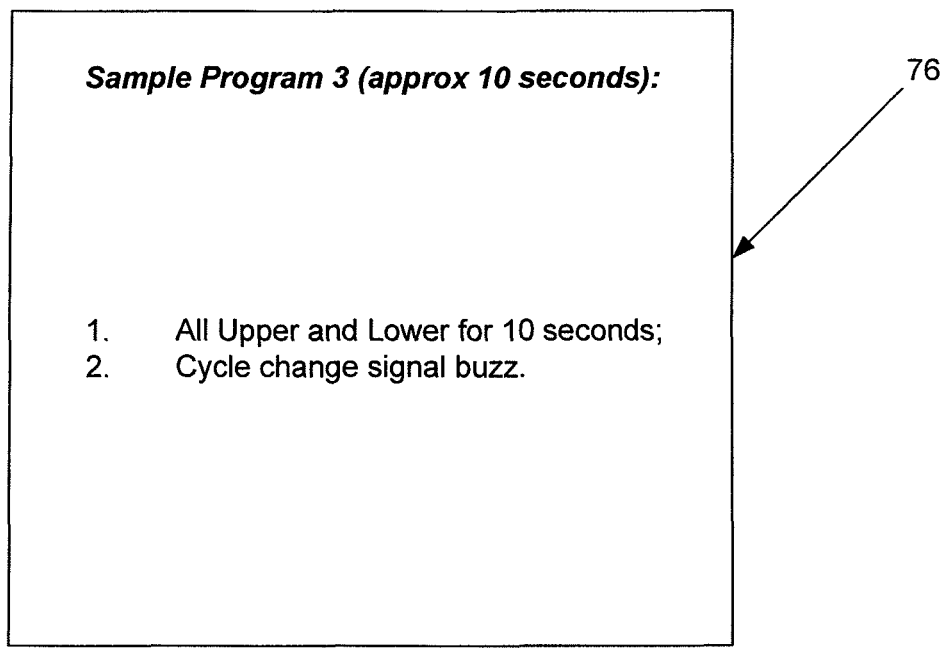

Referring to FIGS. 4A-4C and 5A-5C, various programming configurations are illustrated. In the embodiment of FIG. 4A, a sequential program (72) is configured to work through the brushing of the teeth in six portions (upper left, right, and center; lower left, right, and center). In the depicted embodiment, a cycle change buzz to one or more transducers signals the patient or operator that the cycle is changing to the next stage. Spending approximately 10 seconds at each of the six locations, the program (72) takes approximately one minute to execute. Referring to FIG. 4B, another programming configuration (74) is shown wherein only two stages are used to complete the job: all upper teeth simultaneously, followed by all lower teeth simultaneously, for a cycle of approximately 20 seconds. Referring to FIG. 4C, another programming configuration uses a single actuation stage of all transducers at once to complete the brushing cycle in about 10 seconds. As illustrated in the embodiments of FIGS. 5A-5C, frequency modulation may be utilized in the cleaning process. For example, in the programming embodiment (78) of FIG. 5A, two frequencies may be used sequentially (for example, a low frequency to remove larger bulk plaque, followed by a higher frequency for a polishing effect). The programming embodiment (80) of FIG. 5B shows execution of a first frequency, then a second frequency, then a return to the first frequency (perhaps, low frequency bulk plaque removal, then high frequency polishing, then a return to execute any extra bulk plaque removal). The programming embodiment (82) of FIG. 5C shows execution of three sequential frequencies.

Figure 6A:
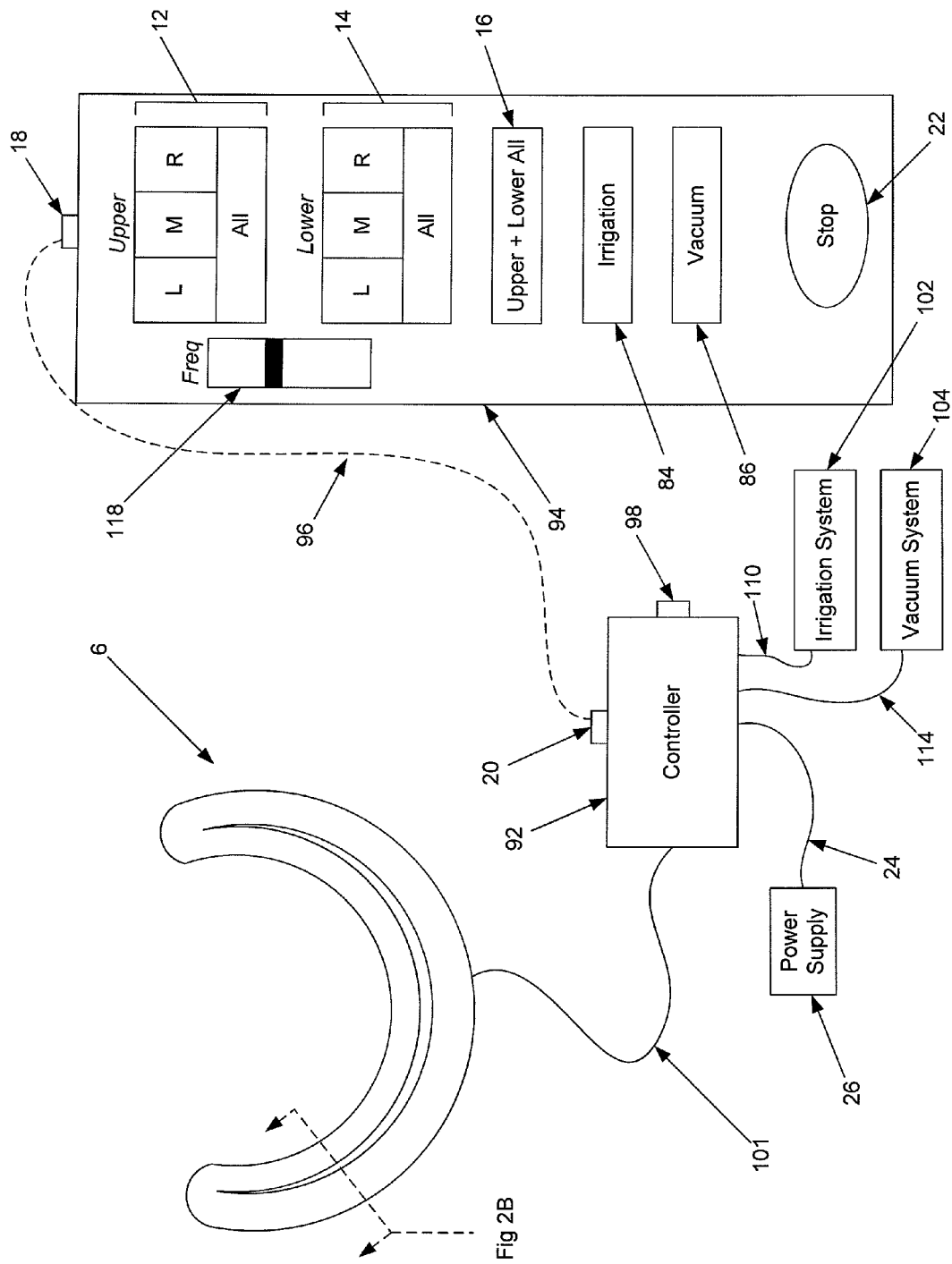
FIG. 6A illustrates one embodiment of a system for automating aspects of the tooth brushing process.
Figure 6B:
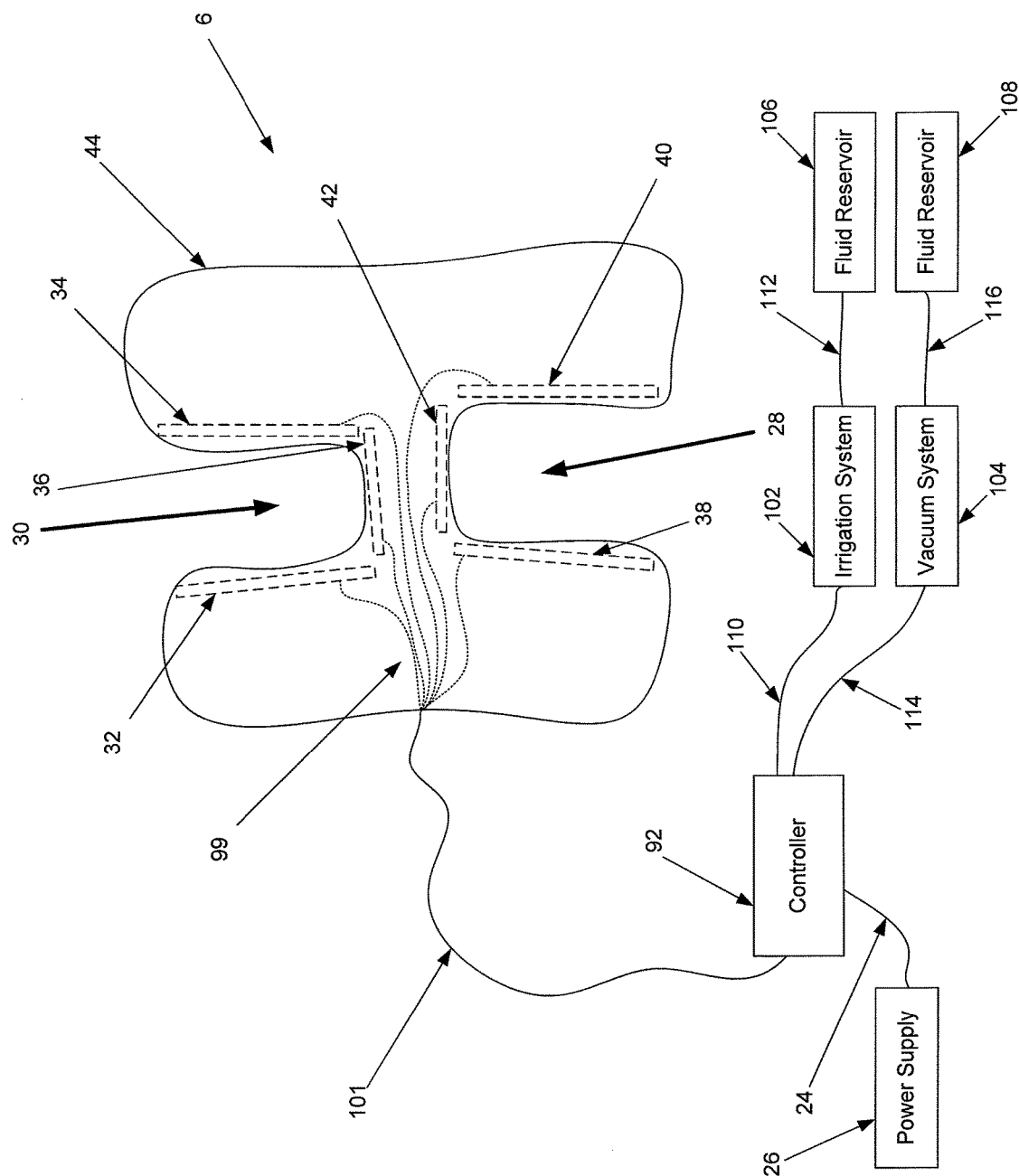
FIG. 6B illustrates a close-up cross sectional view of one embodiment of a system for automating aspects of the tooth brushing process.

Referring to FIGS. 6A and 6B, an embodiment similar to that of FIGS. 2A-2D is depicted, with the exception that irrigation and vacuum functionalities are integrated. The master input device (94) is similar to that of FIG. 2A, but has controls for irrigation (84) and vacuum (86) that are configured to cause an irrigation system (102) to infuse fluid through the coupling lead (101) and into the tray assembly (6) to escape through various pores or lumens formed in the tray assembly (6) and generally configured to infuse fluid into region of the interface between brushing pads and teeth surfaces. A vacuum system (104) may be similarly utilized to evacuate fluid from such sites in the mouth/tray engagement. Referring to FIG. 6B, an infusion fluid reservoir (106) may contain water, fluoride, or other solutions, and may be fluidly coupled (112) to or comprised within the irrigation system (102). The vacuum system may comprise or be fluidly coupled to (116) a fluid reservoir (108) to capture waste fluids evacuated from the brushing area in situ. The controller is operatively coupled (110, 114) via wire leads to the irrigation system (102) and vacuum system (104) to controllably engage and disengage these systems.

Figure 7A:
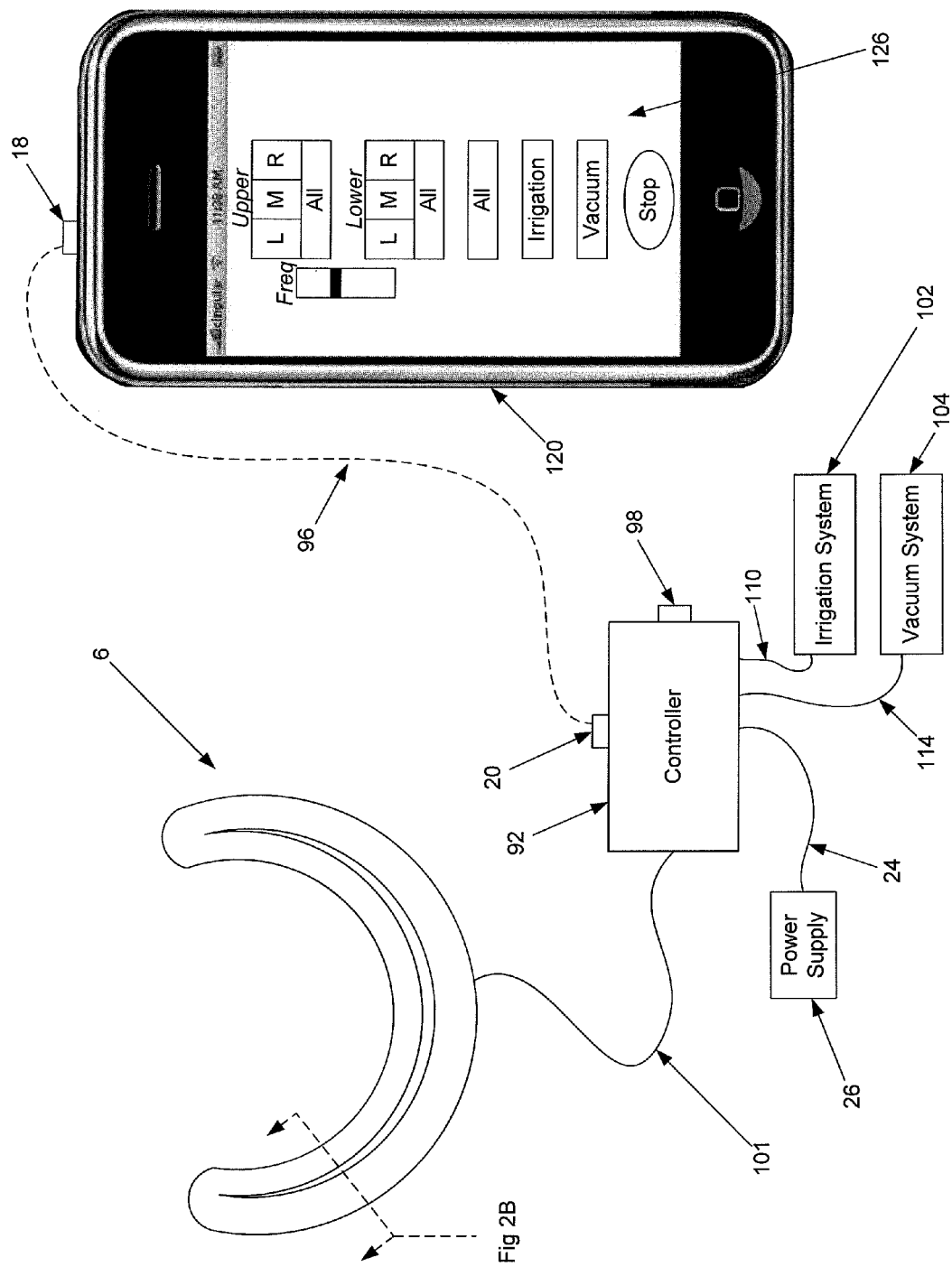
FIG. 7A illustrates one embodiment of a system for automating aspects of the tooth brushing process, wherein a PDA or smartphone device is utilized as a master input device.
Figure 7B:
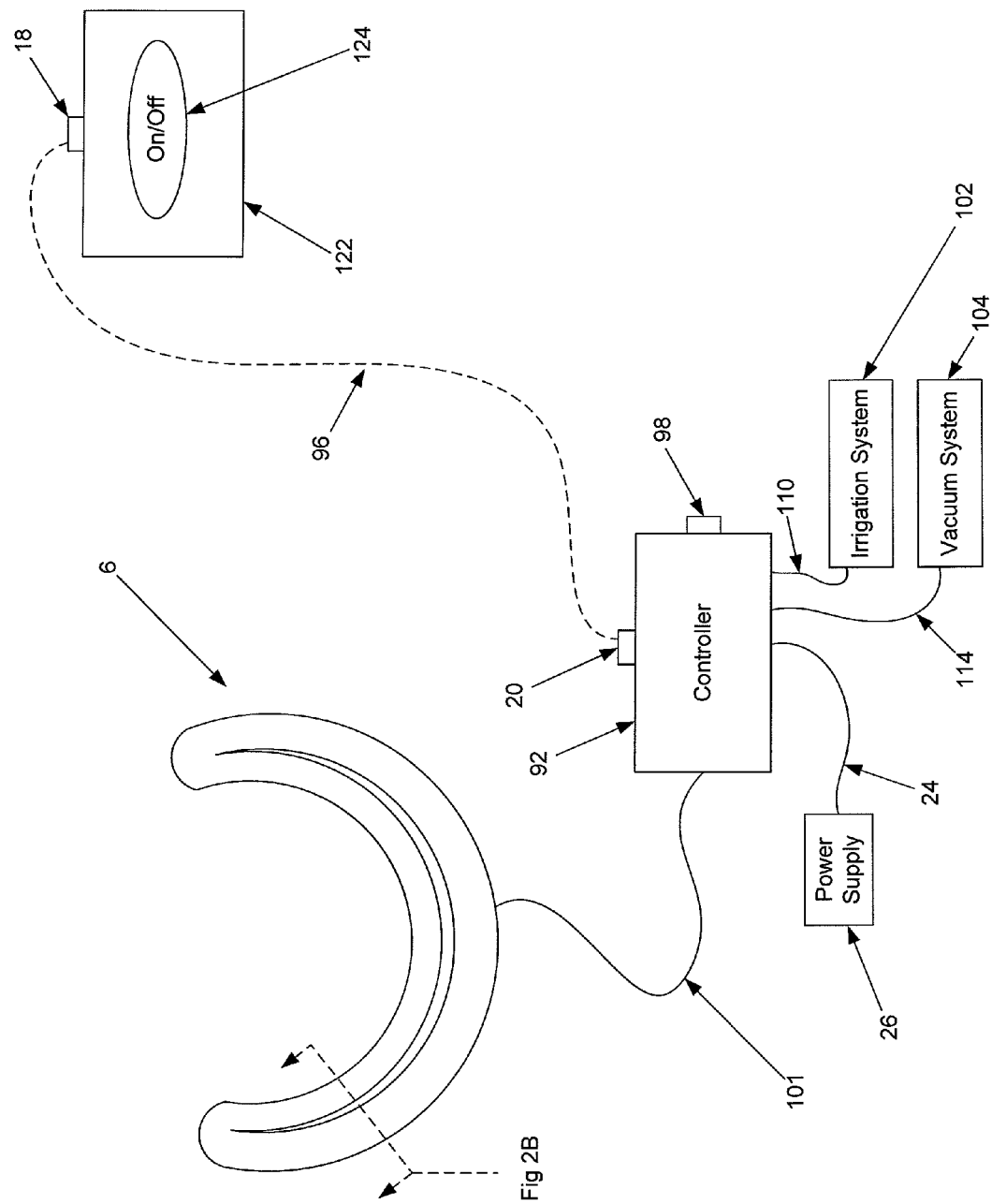
FIG. 7B illustrates one embodiment of a system for automating aspects of the tooth brushing process, wherein the master input device comprises a simple button.

Referring to FIG. 7A, an embodiment is depicted having similar elements as the system depicted, for example, in FIG. 6A, but wherein the master input device (120) comprises a portable electronic device such as a smartphone, PDA, or the like (i.e., such as the product sold by Apple Computer Corp under the tradename iPhone®), that is configured to operate software to produce a graphical user interface comprising digitally presented control buttons (126) for the subject teeth cleaning system. Referring to FIG. 7B, in another embodiment, a master input device (122) may comprise a simple on/off switch or button (124), and referring further to FIG. 7C, this button need not reside on its own mini-console (i.e., as in the embodiment of FIG.

7B)—but rather may reside, for example, coupled to or co-housed with with controller (92).

Figure 7C:
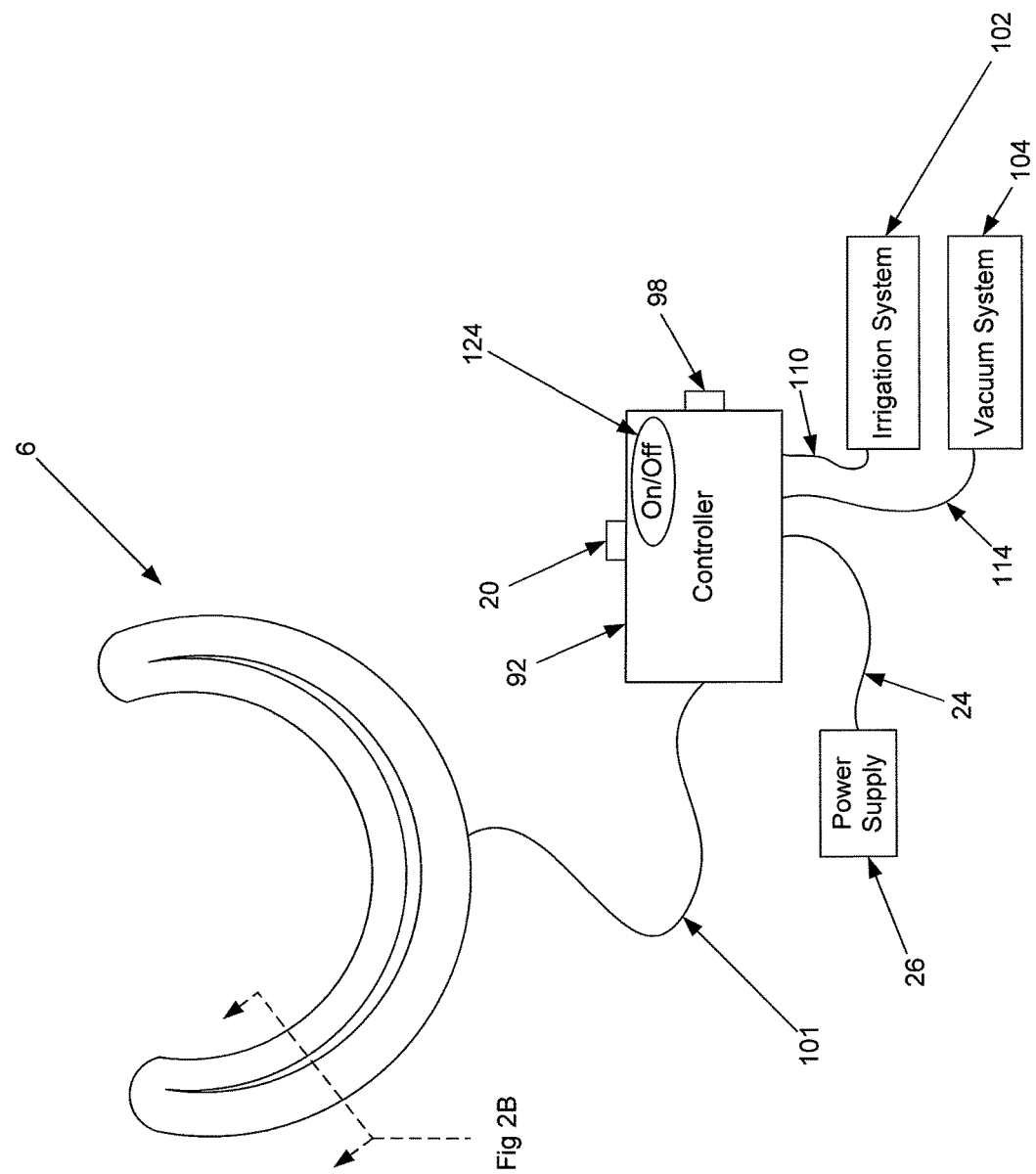
FIG. 7C illustrates one embodiment of a system for automating aspects of the tooth brushing process, wherein the master input device comprises a simple button.
Figure 8A:
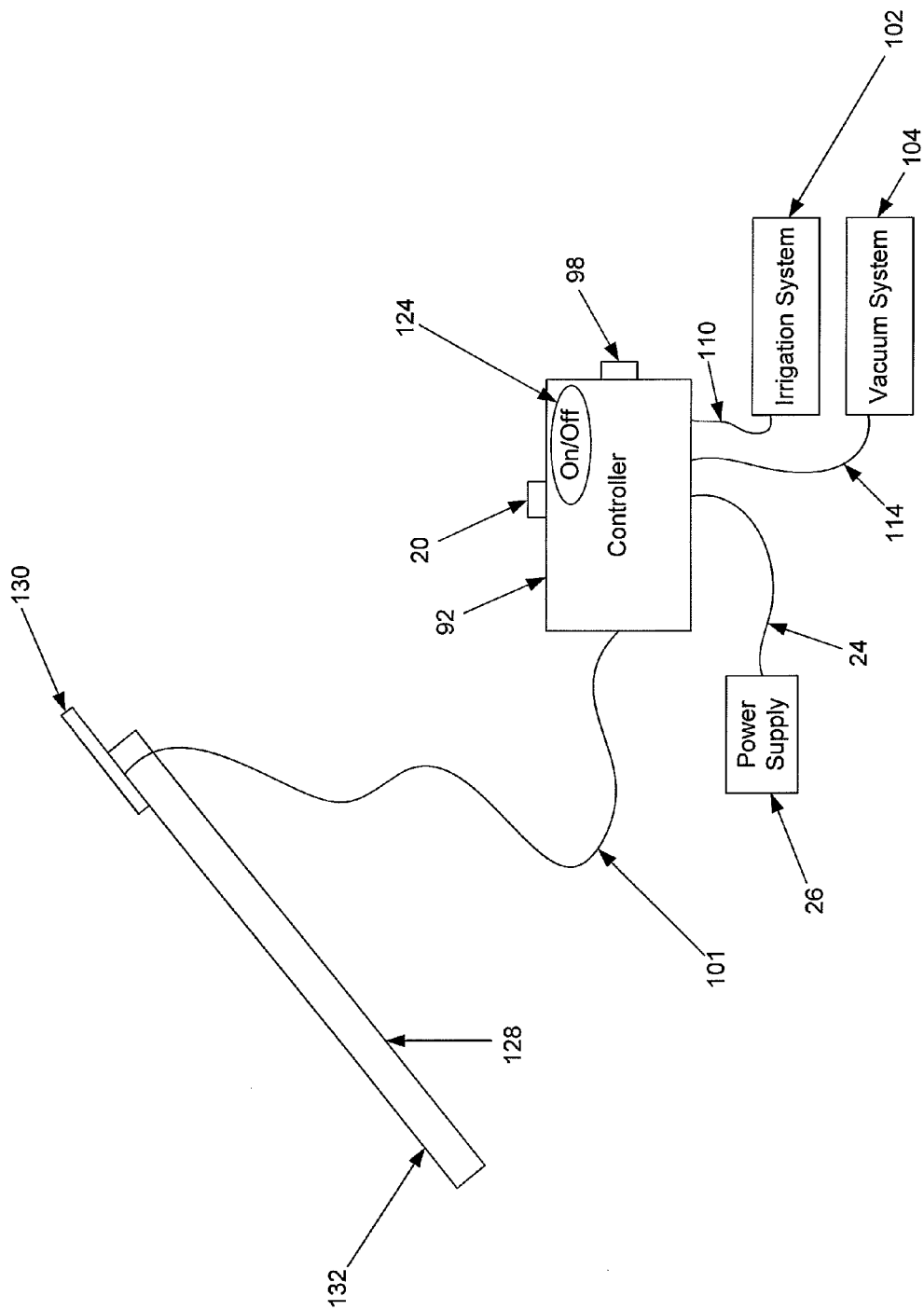
FIG. 8A illustrates one embodiment of a system for automating aspects of the tooth brushing process, wherein a brushing array is coupled to a handle.
Figure 8B:
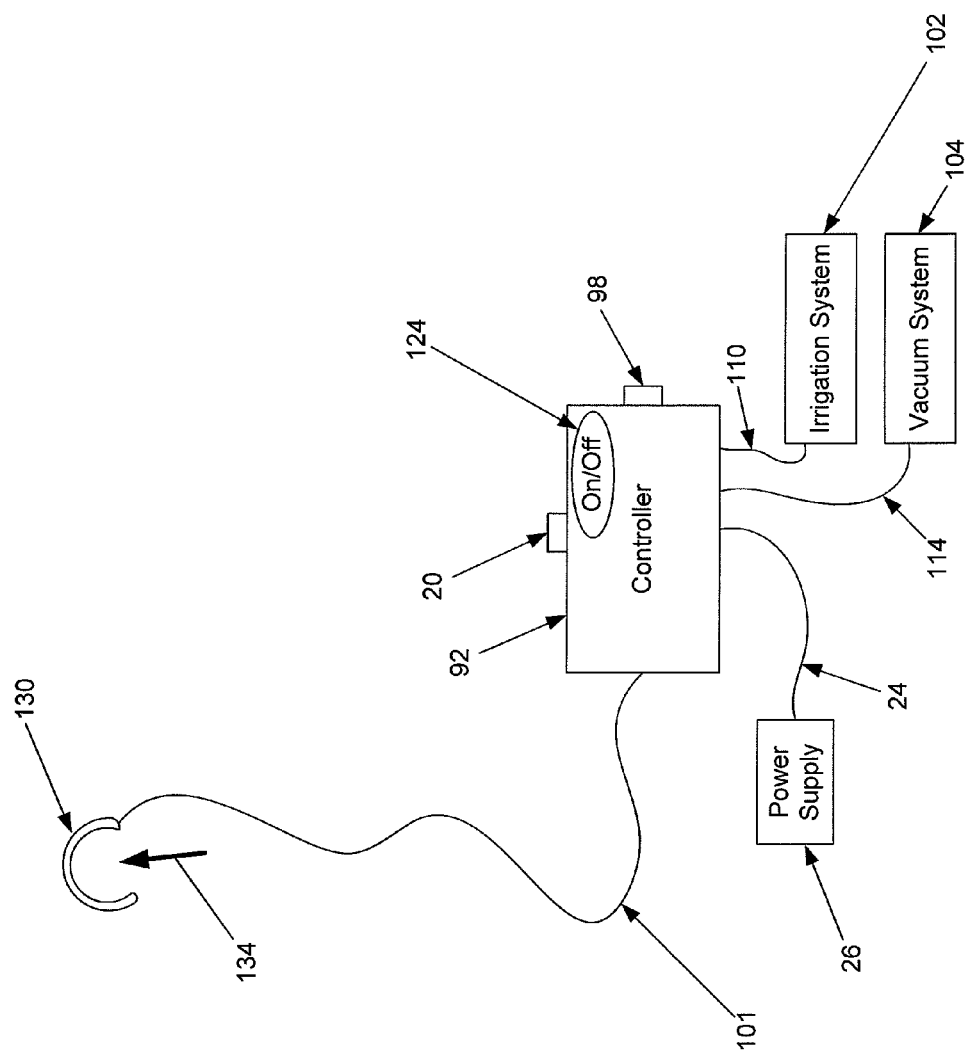
FIG. 8B illustrates one embodiment of a system for automating aspects of the tooth brushing process, wherein a brushing array is configured to be coupled to a finger or tongue.

Referring to FIG. 8A, in another embodiment similar to that of FIG. 7C, a relatively compact brushing array (130), comprising a substrate, and one or more transducers and brushing pads, as in the embodiment described above, may be coupled to a handle (128) and configured such that an operator may grasp the proximal end (132) of the handle (128) and navigate the brushing array (130) around the mouth to brush the teeth, in a manner akin to a tooth brush, but with the advantages of the high frequency cleaning capabilities provided by the subject configuration. The brushing array (130) may be flexible, and may be geometrically sized in a range of sizes: from a relatively small array approximating the size of a dental probe or pick, to a relatively larger size approximately the size of an adult toothbrush bristle array, or longer, to accommodate approximately ⅓ or ½ of the teeth of an operator's upper or lower jaw. The brushing array may be biased to remain relatively straight, or to form a curved shape, such as a concave or convex shape relative to the teeth to which it shall be interfaced. Referring to FIG. 8B, an embodiment similar to that of FIG. 8A is depicted, with the exception that the brushing array (130) in this embodiment is arcuate or curved in a manner to allow engagement (134) of a finger or portion of the human tongue. For example, in one embodiment, a finger may be advanced into a position (134) wherein the array (130) substantially surrounds it, and this combination may be utilized to navigate the mouth of the operator for teeth brushing/cleaning. In another embodiment, the arcuate array may be temporarily coupled to the tongue of the operator, and the tongue may be utilized to navigate, and thereby brush/clean, the nearby teeth.

Figure 9A:
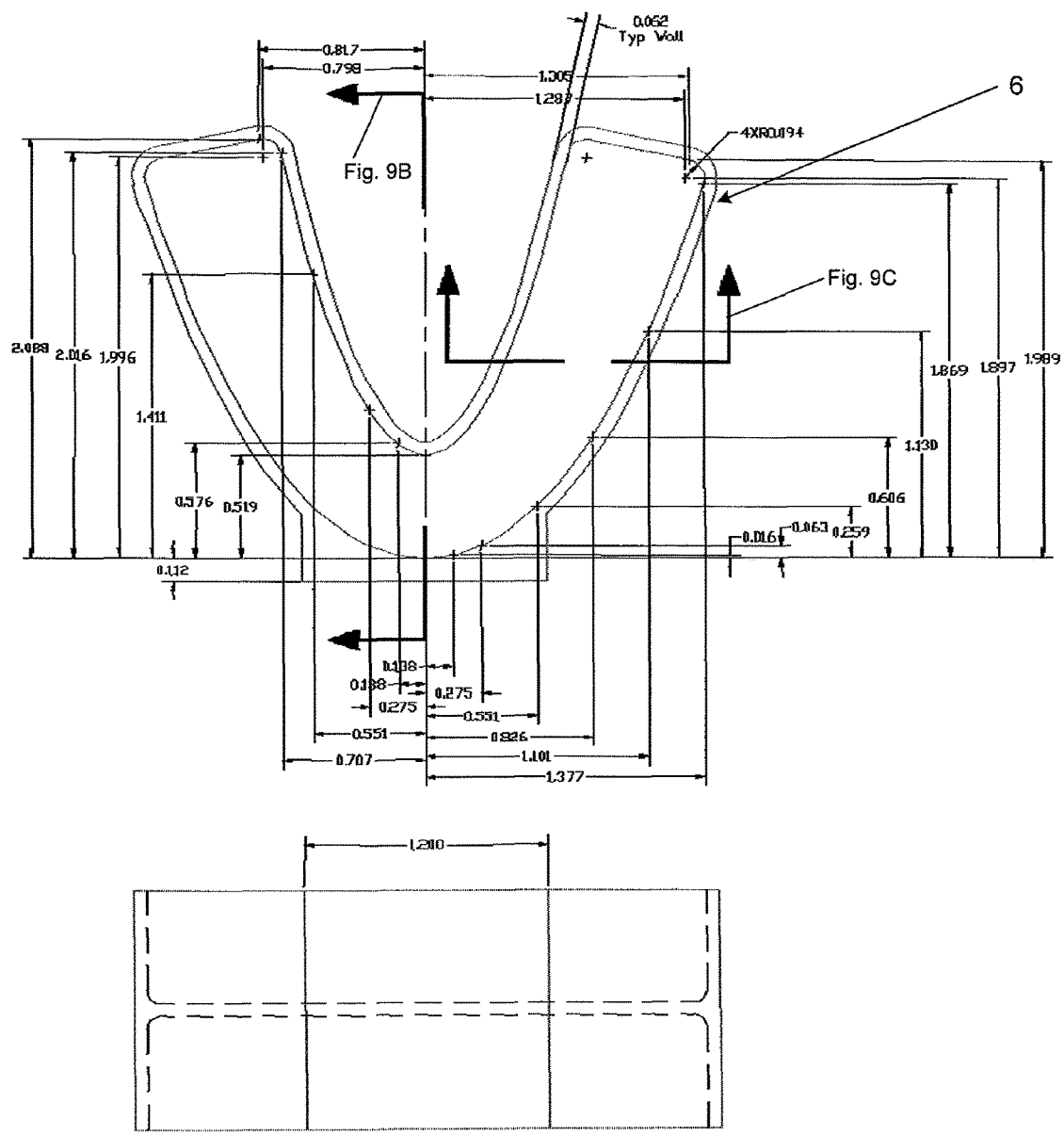
FIGS. 9A-9C illustrate various aspects of a teeth brushing assembly in accordance with the present invention.
Figure 9B:
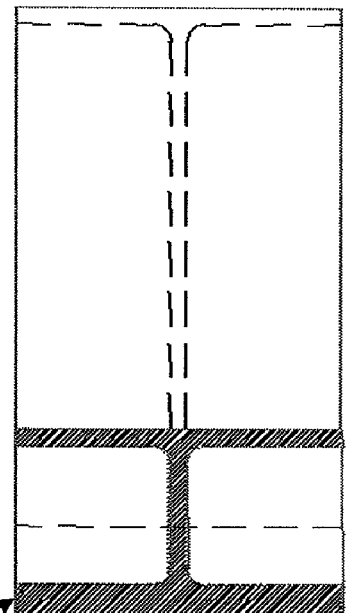
Figure 9C:
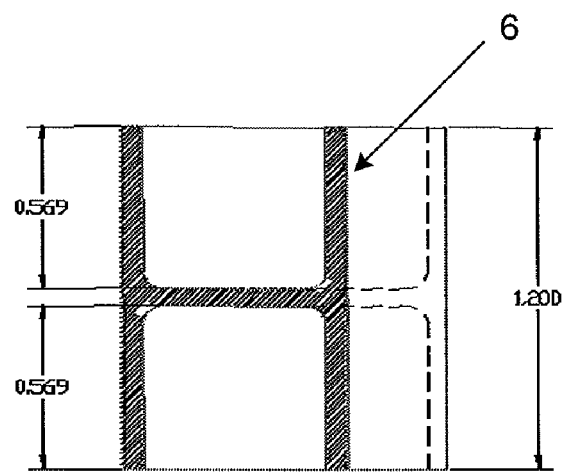
Figure 10B:
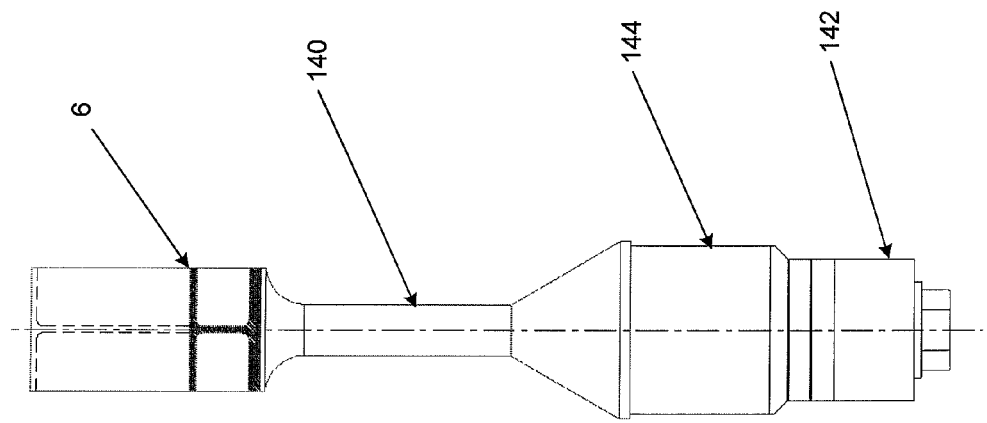
FIGS. 10A and 10B illustrate two views of a teeth brushing assembly with coupled motor pack.
Figure 10A:
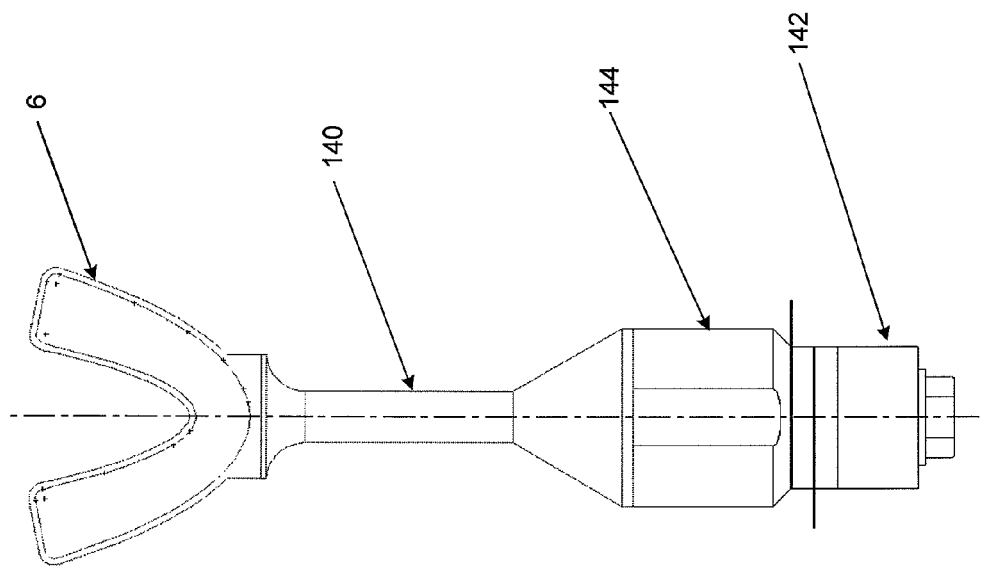
Figure 10C:
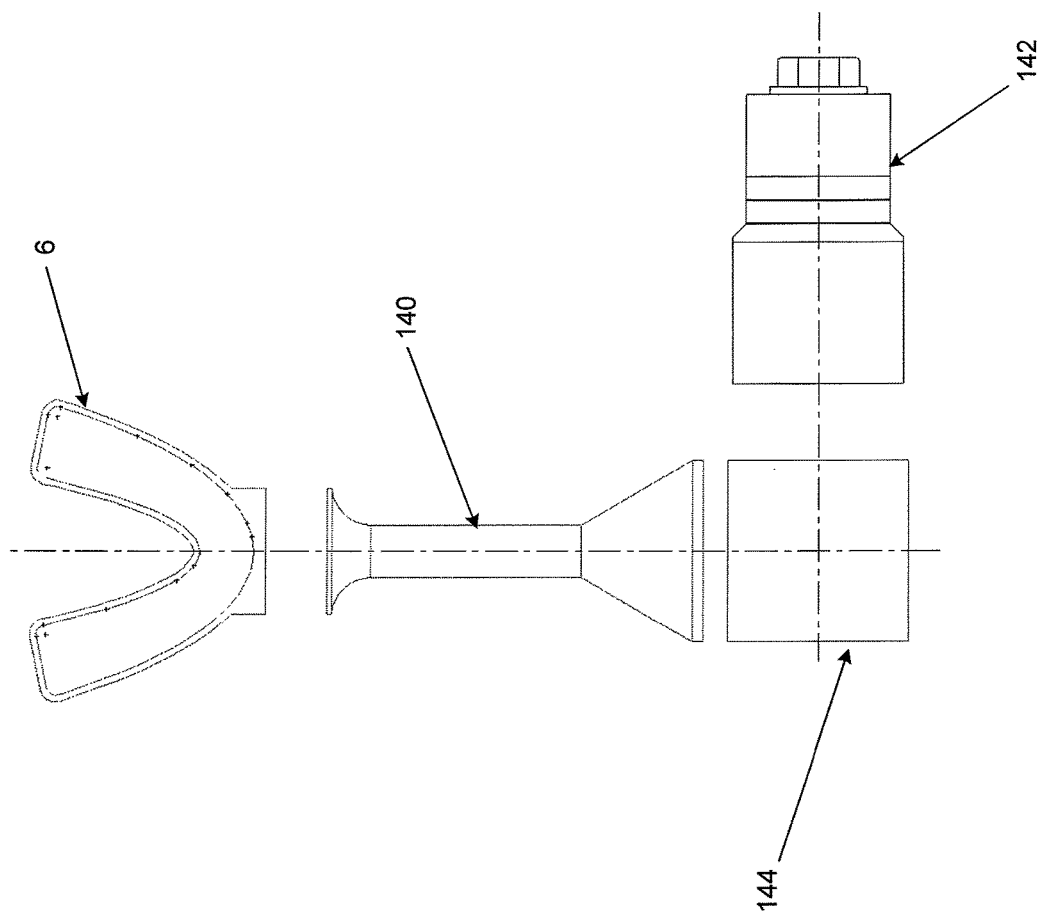
FIG. 10C illustrates a partially exploded view of a teeth brushing assembly with coupled motor pack.

Referring to FIG. 9A, a top view of a thin-walled teeth brushing assembly (6) is depicted with dimensions in inches typical for an adult size. Cross sectional views are shown in FIGS. 9B and 9C. As shown in FIGS. 10A-10C, such an assembly (6) may be removably or fixedly coupled to an all-in-one type of configuration that may be held in one or two hands by the user without additional associated power cords. For example, referring to FIG. 10A, the teeth brushing assembly (6) is removably or fixedly coupled to a gearbox and battery assembly (144) via a handle member (140), which is removably or fixedly coupled to a motor pack (142). FIG. 10B illustrates a view 90 degrees orthogonal to the view of FIG. 10A. FIG. 10C illustrates a partially exploded view of a similar configuration, with the exception that the motor pack (142) is transversely mounted relative to the gearbox/battery assembly (144). With an embodiment such as that shown in FIG. 10A, 10B, or 10C, a user may insert the thin-walled teeth brushing assembly (6) into his or her mouth, controllably engage the motor pack (142), and receive a resultant vibratory/oscillatory motion cleaning of all of his or her teeth simultaneously, as the battery from the battery/gearbox component (144) is configured to activate the motor pack (142), which is configured to operate the gearbox to produce oscillatory/vibratory motion of the handle (140) and associated teeth brushing assembly (6).

Figure 11:
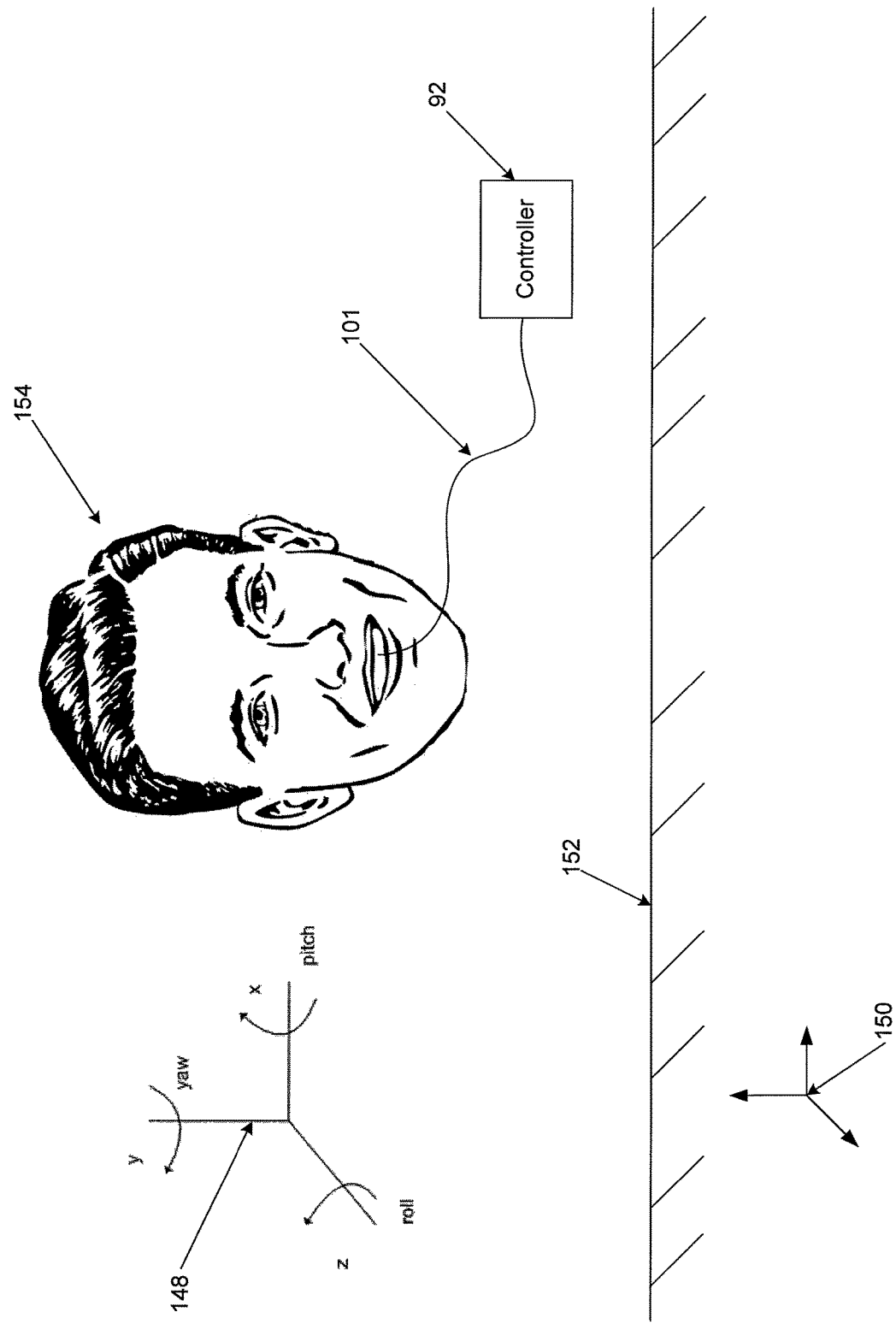
FIG. 11 illustrates a head coordinate system associated with a user's torso. Alternatively a global or ground coordinate system is depicted.

Referring to FIG. 11, two coordinate systems (148, 150) are illustrated relative to the user's head (154). A global coordinate system (150) is defined as the coordinate system of the ground or floor (152) around the user. A torso coordinate system (148) is defined as the coordinate system associated with the user's torso as he stands in a room relative to the ground. One of the challenges associated with efficient small amplitude vibratory teeth brushing as described herein is maintaining adequate irrigation medium, or fluid, between the brushing surfaces of the teeth brushing assembly (6) and the subject teeth. One of the most straightforward ways of facilitating localized pooling of irrigation fluid to targeted portions of the subject teeth is with the help of gravity. For example, the teeth of the mouth may be divided into groupings such as: upper versus lower; lower left molars, lower incisors, lower right molars, upper right molars, upper incisors, upper right molars (canines being on the borders of the latter grouping), etc. To focus irrigation pooling near the incisors, the user may pitch his head forward relative to the torso coordinate system (148), and depending upon the level of such pitch rotation, focus the irrigation pooling adjacent the lower incisors, both upper and lower incisors, or the upper incisors. Similarly, to focus irrigation pooling near the molars, the user may yaw rotate his neck while also pitching it relative to the torso coordinate system (148) in various configurations to direct irrigation pooling to various locations of the molars, pre-molars, canines, etc. Referring to FIGS. 12-17, several embodiments for operating variations of the subject invention are illustrated.

Figure 12:
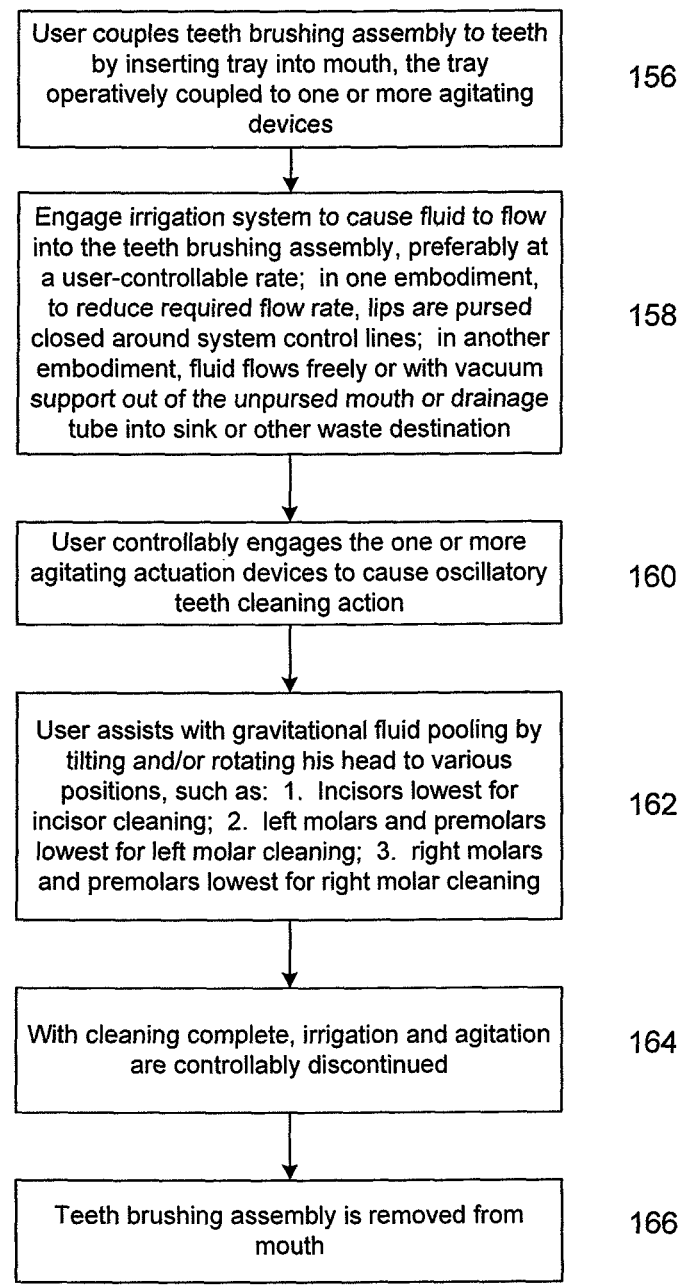
FIG. 12 illustrates a process for cleaning teeth in accordance with one embodiment of a system for automating aspects of the tooth brushing process.

Referring to FIG. 12, after a user couples a teeth brushing assembly to his teeth by inserting a tray into his mouth, the tray comprising or being operatively coupled to one or more electromechanical agitating devices (156), the irrigation system may be engaged (158) to cause fluid to flow into the teeth brushing assembly, preferably at a rate that may be controlled by the user with a master input device, controller knob/interface, or the like. In one embodiment, to reduce the amount of fluid flow required, the user's lips may be pursed around the system control lines (or handle in an all-in-one embodiment similar to that depicted in FIGS. 10A-10C); in another embodiment, the user may allow fluid to freely flow out of his mouth, or through a drain or vacuum line. The user may then (or simultaneously with engagement of the irrigation system in another embodiment) engage the one or more agitating actuation devices to cause oscillatory teeth cleaning action (160). The user may assist with gravitational fluid pooling by tilting and/or rotating his head to various positions (162), such as: 1) incisors gravitationally lowest for incisor cleaning; 2) left molars gravitationally lowest for left molar cleaning; 3) right molars gravitationally lowest for right molar cleaning; premolars and canines in the overlap between these divisions of the mouth. With the cleaning complete, irrigation and agitation may be controllably discontinued (164), such as by the push of a user interface button or expiration of a discrete timer time window, and the teeth brushing assembly removed from the mouth (166).

Figure 13:
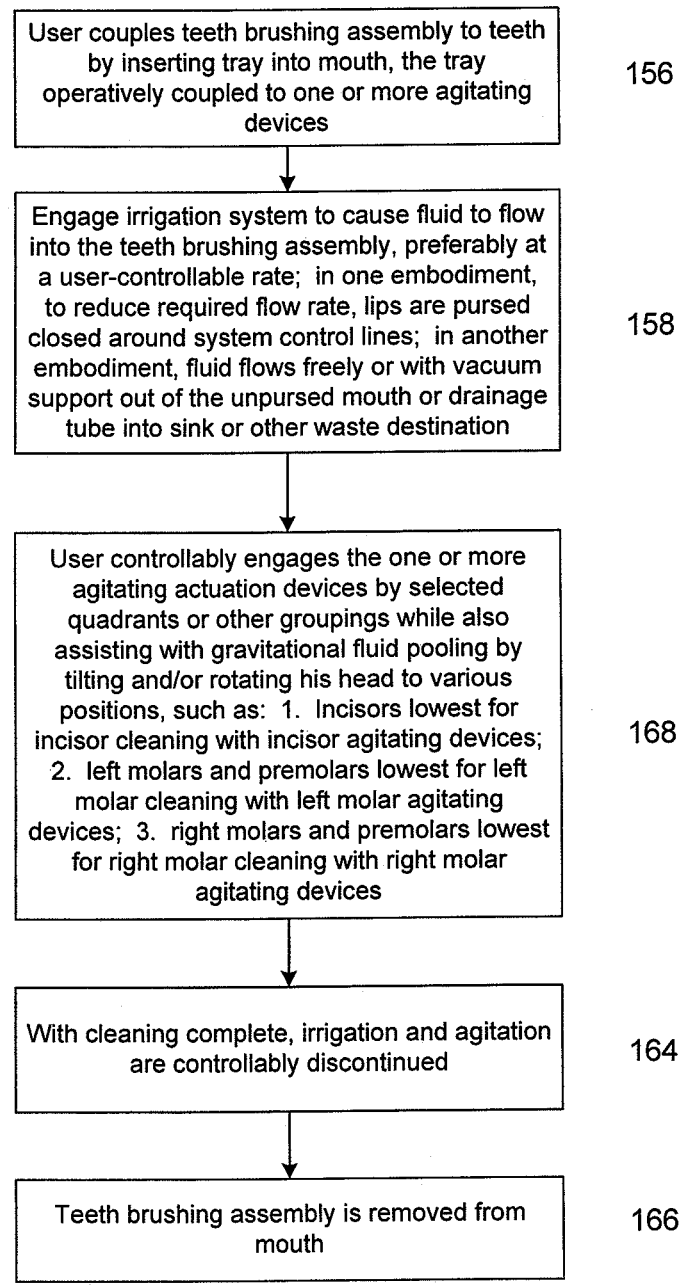
FIG. 13 illustrates a process for cleaning teeth in accordance with one embodiment of a system for automating aspects of the tooth brushing process.

Referring to FIG. 13, a technique and configuration similar to that illustrated in FIG. 12 is depicted, with the exception that the user may controllably engage the agitating actuation devices by selected quadrants or other groupings while also assisting with gravitational fluid pooling by tilting and/or rotating his head to various positions (168). In other words, rather than agitating the entire mouth worth of teeth simultaneously, the user may agitate only a focused subportion of the teeth, such as the portion that is receiving the irrigation pooling subject to his head/jaw orientation.

Figure 14:
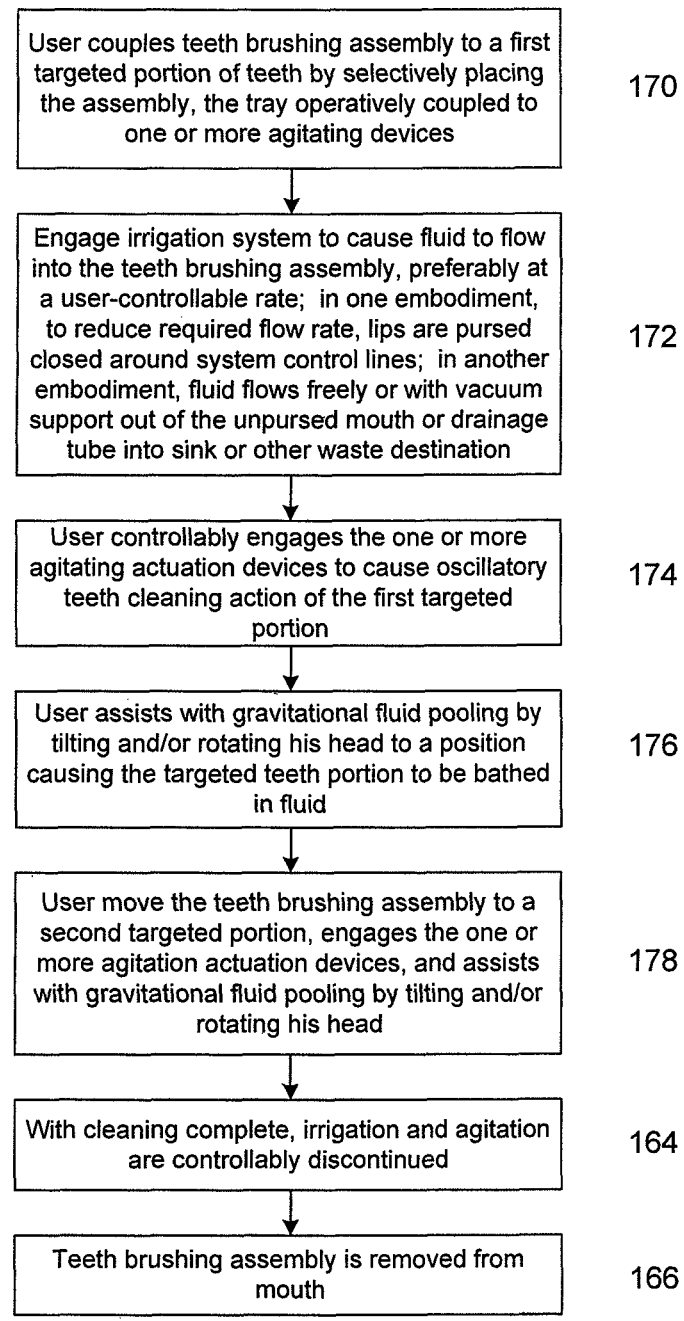
FIG. 14 illustrates a process for cleaning teeth in accordance with one embodiment of a system for automating aspects of the tooth brushing process.

Referring to FIG. 14, a user may operate a teeth brushing assembly configured to be focused upon a targeted portion of the overall set of teeth, akin to a toothbrush (170). The irrigation system may be controllably engaged (172), along with the agitating actuation (174), which may be interrupted during moves of the brushing assembly—or alternatively left on during such moves. The user may assist with irrigation focusing/pooling (176), and the user may move (i.e., with his hands akin to the manner in which a toothbrush is moved) the brushing assembly to other positions in the mouth (178).

Figure 15:
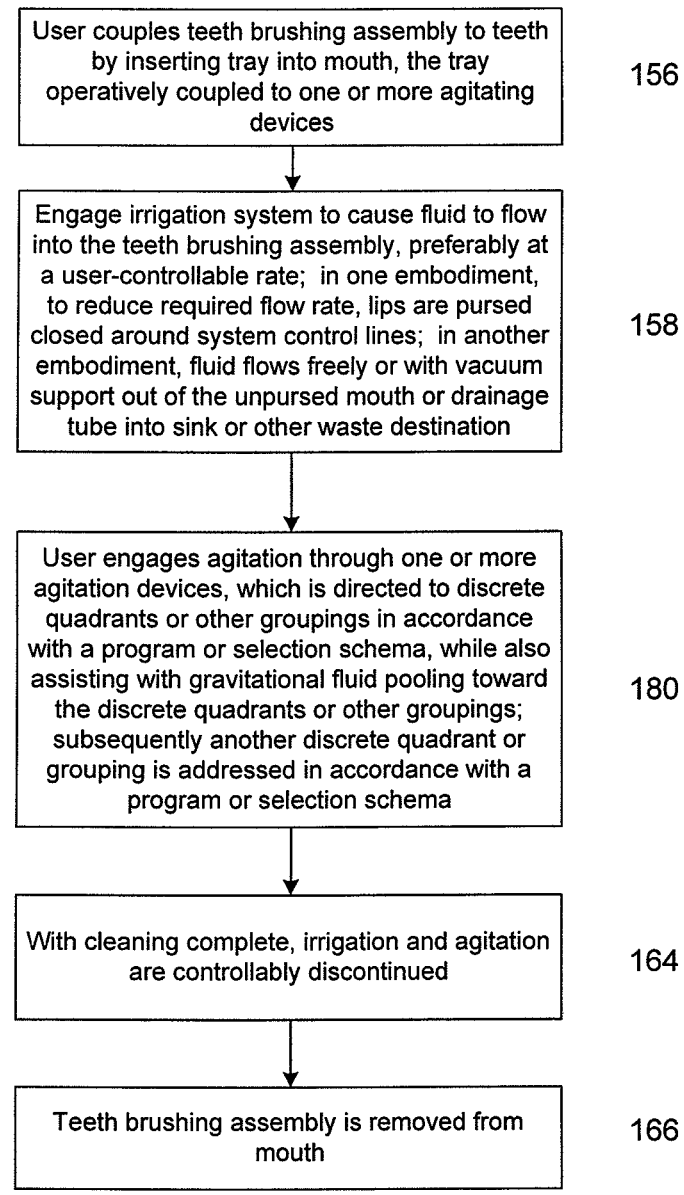
FIG. 15 illustrates a process for cleaning teeth in accordance with one embodiment of a system for automating aspects of the tooth brushing process.

Referring to FIG. 15, an embodiment similar to that of FIG. 13 is illustrated, with the exception that the agitation is directed through the tray to various sub-portions of the teeth of the mouth in accordance with a predetermined program or selection schema (for example: bottom first—left, front, right; top last—left, front, right; see aforementioned programming configurations) (180).

Figure 16:
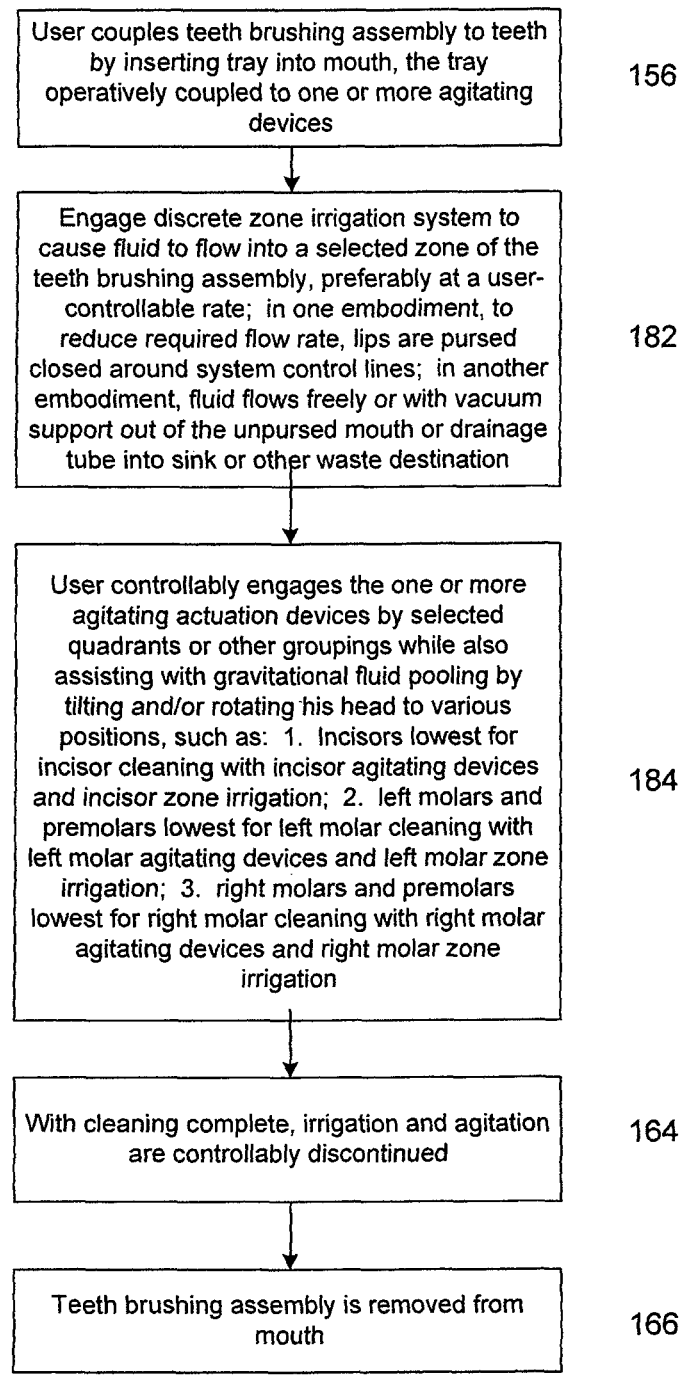
FIG. 16 illustrates a process for cleaning teeth in accordance with one embodiment of a system for automating aspects of the tooth brushing process.

Referring to FIG. 16, after the teeth cleaning assembly tray has been inserted in the user's mouth (156), a discrete zone irrigation configuration may be utilized (182) to direct irrigation to selected sub-portions of the teeth, which may be changed over time. In other words, the mouth may be broken up into a plurality of targeted zones, each of which receives zone irrigation (182) and zone agitation (184) during a selected portion of the overall brushing time, in accordance with user selections regarding targeted zones.

Figure 17:
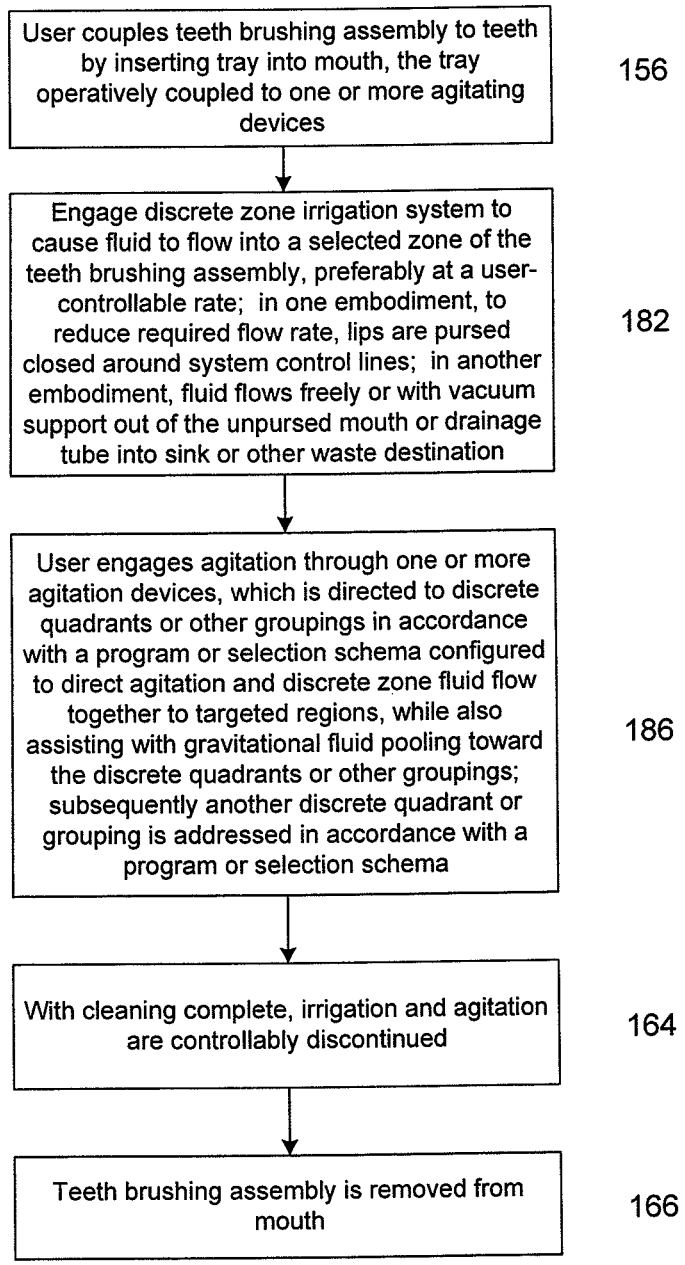
FIG. 17 illustrates a process for cleaning teeth in accordance with one embodiment of a system for automating aspects of the tooth brushing process.

Referring to FIG. 17, an embodiment similar to that of FIG. 16 is illustrated, with the exception that with the embodiment of FIG. 17, zone alternating/selection (i.e., the order and timing in which each zone becomes the operative zone for irrigation and agitation) is controlled using a predetermined programming or selection schema (186) which may, for example, be at the recommendation of the user's dentist of dental hygienist.

Figure 18A:
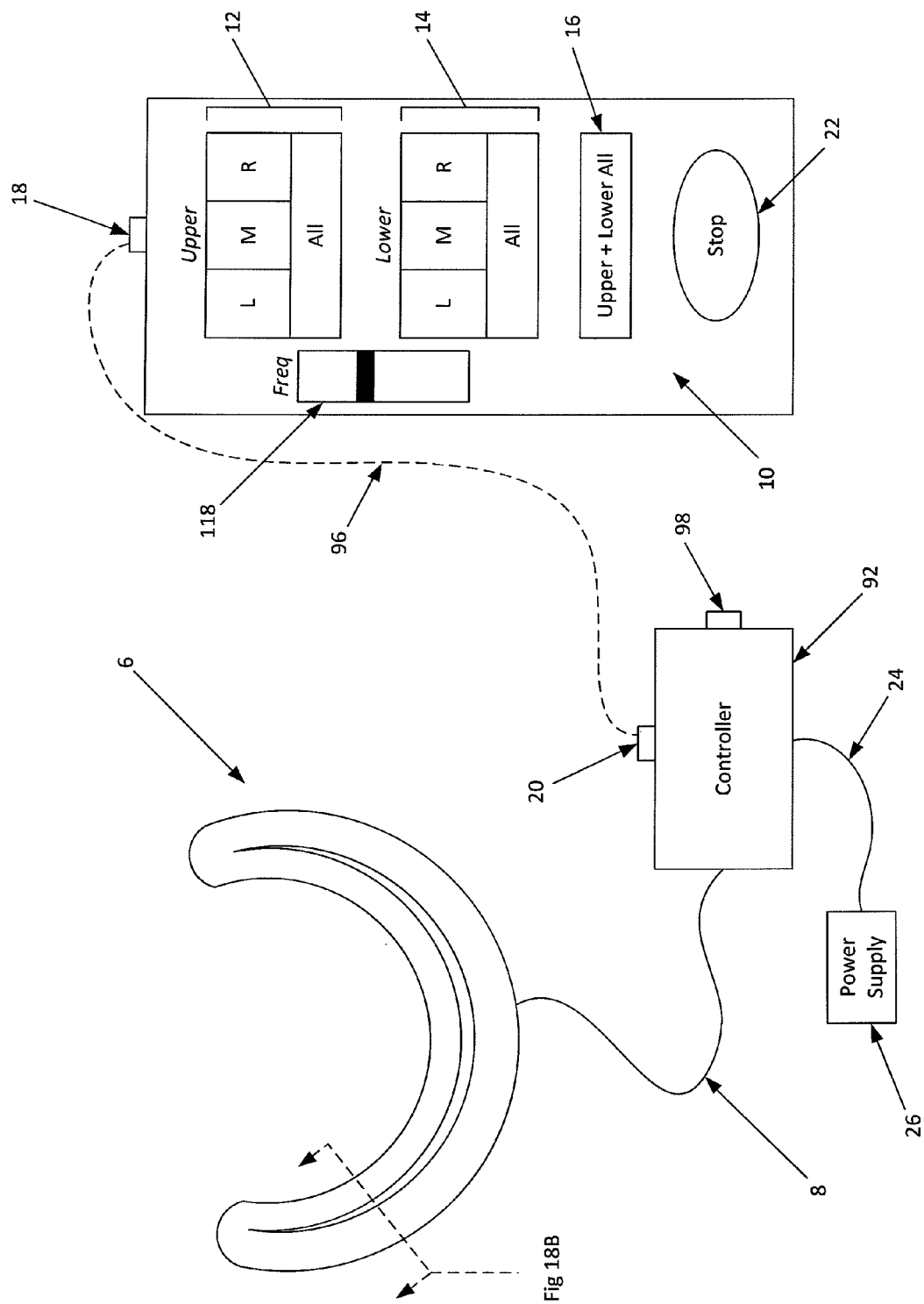
FIG. 18A illustrates one embodiment of a system for automating aspects of the tooth brushing process.
Figure 18B:
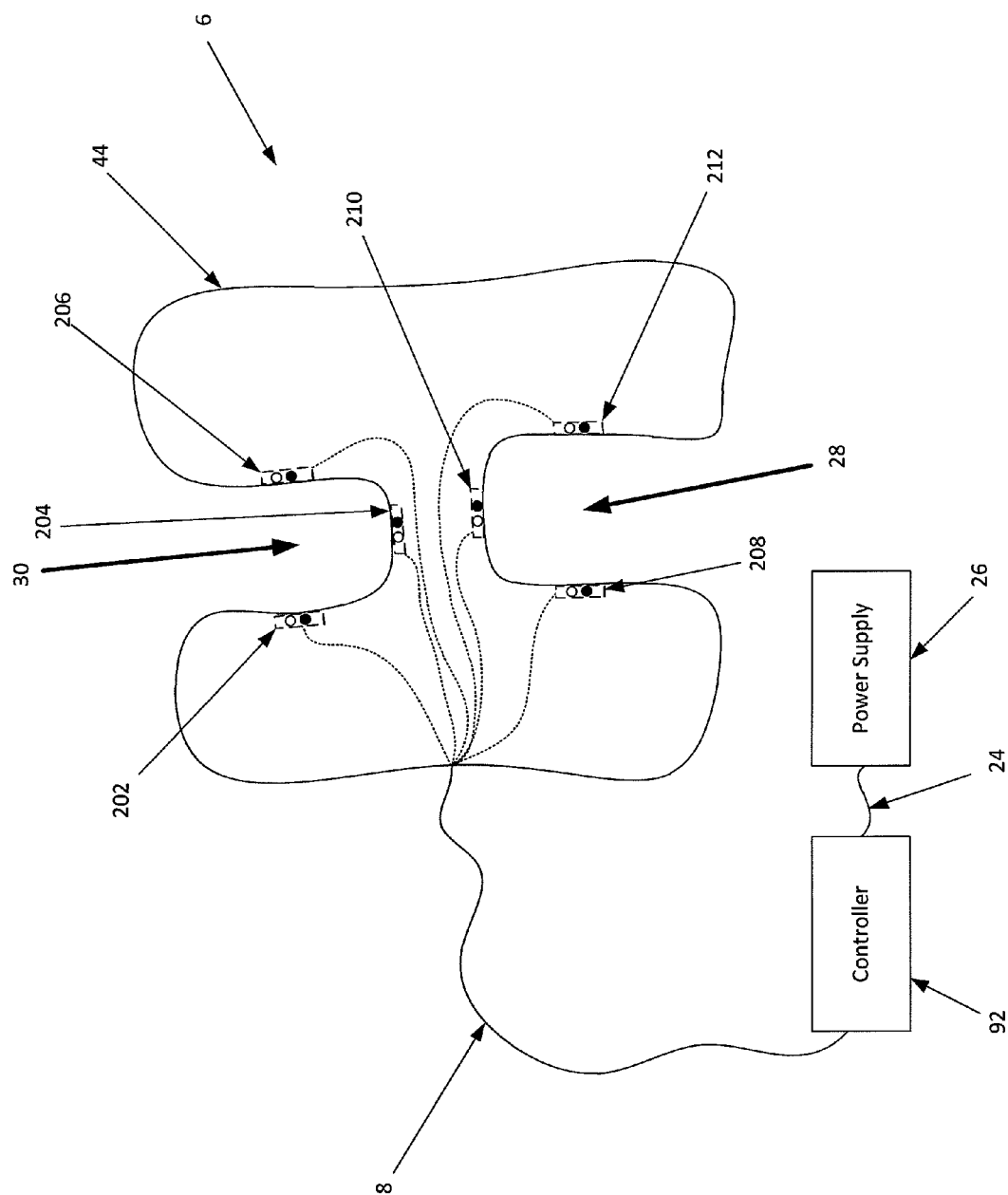
FIG. 18B illustrates a close-up cross sectional view of one embodiment of a system for automating aspects of the tooth brushing process.
Figure 18C:
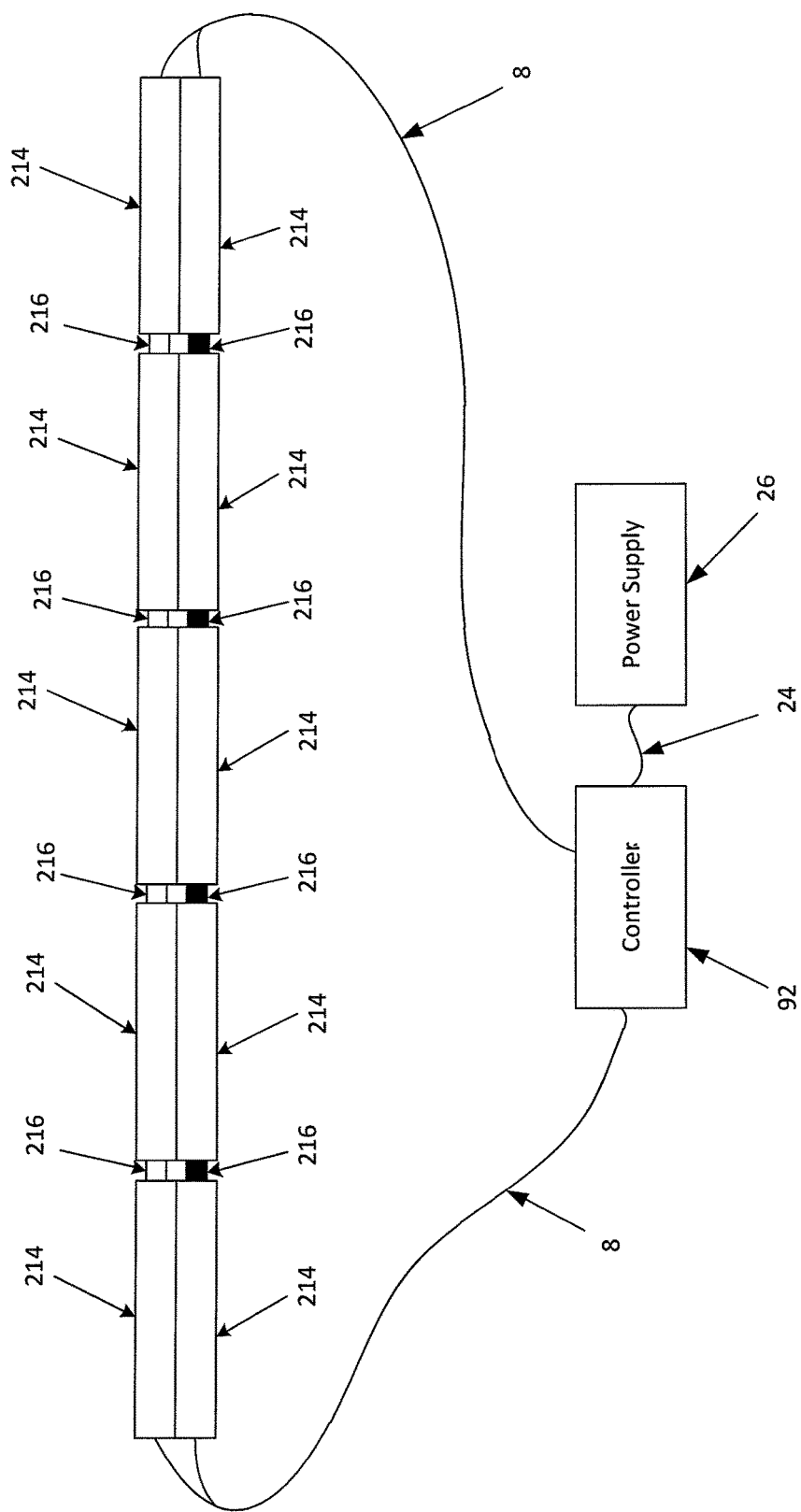
FIG. 18C depicts a close-up side view of a shockwave electrode configuration a system for automating aspects of the tooth brushing process.
Figure 19:
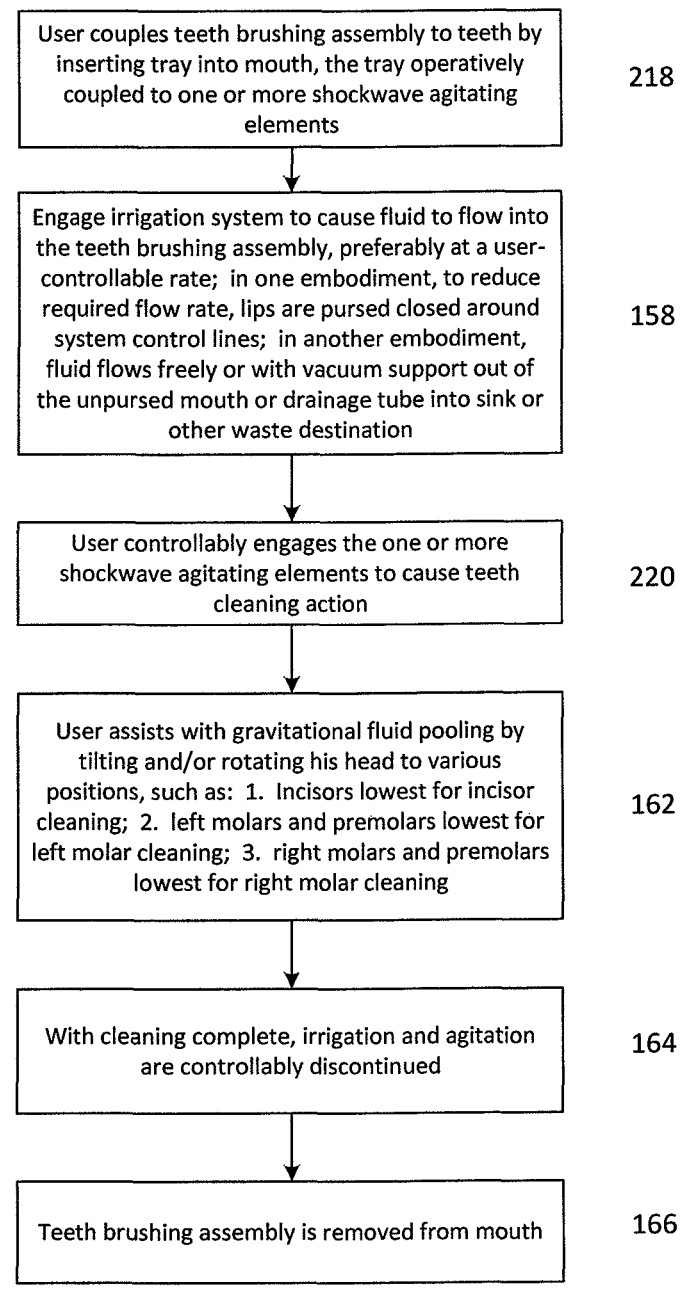
FIG. 19 illustrates a process for cleaning teeth in accordance with one embodiment of a system for automating aspects of the tooth brushing process.

Referring to FIGS. 18A-19, another embodiment is illustrated, wherein a different agitating element may be utilized to break loose plaque and other deposits from teeth in an effort to clean such teeth: a shockwave electrode pair or shockwave transducer. Referring to FIG. 18A, a system similar to that depicted in FIG. 2A is shown with a teeth brushing assembly comprising a flexible tray element (44) which is shown in detailed cross section in FIG. 18B. Referring to FIG. 18B, in place of the agitating pads (32, 34, 36, 38, 40, 42) of the embodiments of FIG. 2B or 6B, the embodiment of FIG. 18B has shockwave transducer elements or shockwave electrode pairs (202, 204, 206, 208, 210, 212) which are configured to create shockwaves that are transmitted toward the associated teeth to break loose plaque and other deposits from teeth in an effort to clean such teeth. In one embodiment, each of the shockwave transducer elements (202, 204, 206, 208, 210, 212) is coupled to the flexible substrate material (44) in a position wherein direct or nearly direct transfer of shockwave energy to associated teeth may be accomplished. As discussed above in reference to FIG. 2B, the tray is configured such that the teeth are placed into, and at least partially surrounded by, the tray in locations labeled with elements 30 and 28, which may also be denominated as "slots" for the teeth. With a shockwave agitation embodiment, the slots may be lined or at least partially filled with a transmissive medium or material, such as a fluid (i.e., water) or viscous gel (i.e., a tooth-cleaning paste with relatively low-viscosity as compared with conventional toothpastes), that is configured to optimally transmit shockwaves from the transducers (202, 204, 206, 208, 210, 212) to the associated teeth. Further, in one embodiment, the materials surrounding the shockwave transducers (202, 204, 206, 208, 210, 212) in directions that are not adjacent the targeted teeth may be configured to absorb or reflect shockwaves—to assist in focusing the shockwave energy upon the desired targeted teeth and not other structures in the mouth or in the device itself. In the depicted embodiment, one shockwave transducer is provided for each of the three exposed sides of an associated tooth. In another embodiment, one shockwave transducer may be configured to provide adequate disruption of plaque or other debris, such as the slot base pair or transducers (204, 210) shown in the embodiment of FIG. 18B. In other embodiments, more than three shockwave transducers may be provided for each of the associated teeth. Each of the shockwave transducers or shockwave electrode pairs (202, 204, 206, 208, 210, 212) may comprise a pair of exposed electrode portions that are biased to produce a brief short circuit when electrified, causing a shockwave local to the exposed electrode portions. Shockwave technology has been utilized in other medical applications, such as lithotripsy applications described in U.S. Published patent application Ser. No. 12/436,547 to Mantell et al, which is incorporated by reference herein in its entirety. Referring to FIG. 18C, to illustrate one configuration for producing a series of shockwave transducers or electrode pairs, a close up side view of a pair of continuous lead wires (8) that are mostly insulated from each other by insulative layering (214) is depicted in a linear (i.e., not arcuate or curved, as would be the case when such a configuration is embedded into a flexible teeth tray substrate such as that depicted in FIG. 18A as element 6). At a desired distance longitudinally, discontinuities (214) have been created in the insulative layer, which result in a series of shockwave electrode pairings (i.e., each electrode formed by a gap in the insulative layering that places the polar opposite leads in electrical access to each other, to create a short circuit when the lead pair is electrified—somewhat like a series of small spark plugs) that may be utilized to generate a series of associated shock waves, as facilitated by the intercoupled controller (92) and power supply (26). In one embodiment, the discontinuities may be created in the insulative layering at a pitch configured to place one electrode (i.e., one discontinuity) at the longitudinal position of each tooth of the patient/person. In another embodiment, discontinuities may be placed at a higher pitch, such as every few millimeters, or at a greater pitch. In another embodiment, flex circuit or flexible circuit substrate technology may be utilized to manufacture the electrode strings.

Referring to FIG. 19, a process for cleaning teeth with a system such as that described in reference to FIGS. 18A-18C is depicted; such a process is similar to that shown in FIG. 12, with the exception that the electromechanical agitating pads have been replaced with shockwave agitating elements (218, 220). Similarly, each of the embodiments described in reference to FIGS. 13-17 may be adapted for shockwave agitation with shockwave transducer elements in place of the electromechanical agitating pads. Other hybrid embodiments may incorporate both electromechanical agitation and shockwave agitation.

While embodiments described above, such as those of FIGS. 2A-2D, 6A-7C, feature flexible substrate (44) materials for the main tray assembly (6), other embodiments may comprise substantially rigid or nonflexible substrate materials to retain predetermined tray geometry with a high level of precision, and may have coatings or outer layers that are at least somewhat flexible or pliable to accommodate atraumatic tissue interaction.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A system for brushing the teeth of a person, comprising:
   a vibratory transducer coupled to a brushing panel; and
   a controller operatively coupled to the vibratory transducer,
   wherein subject to an input from an operator, the controller is configured to cause a first reciprocating brushing motion of the brushing panel against a surface of a tooth at a first frequency, followed by a second reciprocating brushing motion of the brushing panel against the surface of the tooth at a second frequency different from the first frequency, to clean the tooth.

2. The system of claim 1, wherein the second frequency is higher than the first frequency.

3. The system of claim 2, wherein the first reciprocating brushing motion at the first frequency is configured to remove plaque from the tooth.

4. The system of claim 2, wherein the second reciprocating brushing motion at the second frequency is configured to polish the tooth.

5. The system of claim 1, wherein the controller is configured to cause the first reciprocating brushing motion at the first frequency for a first period of time and the second reciprocating brushing motion at the second frequency for a second period of time.

6. The system of claim 1, wherein the controller is configured to cause a third reciprocating brushing motion of the brushing panel against the surface of the tooth at the first frequency after the second reciprocating brushing motion.

7. The system of claim 6, the controller is configured to cause the third reciprocating brushing motion at the first frequency for a third period of time.

8. The system of claim 1, wherein the controller is configured to cause a third reciprocating brushing motion of the brushing panel against the surface of the tooth at a third frequency different from the first frequency and the second frequency after the second reciprocating brushing motion.

9. The system of claim 8, the controller is configured to cause the third reciprocating brushing motion at the third frequency for a third period of time.

10. The system of claim 1, further comprising a master input device operatively coupled to the controller and configured to receive a command from the operator and deliver a control signal to the controller.

11. The system of claim 1, wherein the vibratory transducer comprises a piezoelectric transducer.

12. The system of claim 11, wherein the piezoelectric transducer is configured to oscillate at ultrasonic frequencies.

13. The system of claim 1, wherein the brushing panel comprises a substrate panel coupled to a brushing media.

14. The system of claim 13, wherein the substrate panel is removably coupled to the vibratory transducer.

15. The system of claim 14, wherein an interference fit clip fitting is utilized to removably couple the substrate panel to the vibratory transducer.

16. The system of claim 13, wherein the substrate panel is fixedly coupled to the vibratory transducer.

17. The system of claim 13, wherein the brushing media comprises one or more flexible bristles.

18. The system of claim 17, wherein the one or more flexible bristles comprise a natural fiber.

19. The system of claim 17, wherein the one or more flexible bristles comprise a manufactured fiber.

20. The system of claim 1, further comprising a flexible teeth tray configured to at least partially encapsulate one or more of the teeth in a flexible substrate material, the flexible teeth tray comprising the vibratory transducer removably coupled to the brushing panel.

* * * * *